(12) United States Patent
Cruz et al.

(10) Patent No.: US 11,753,358 B2
(45) Date of Patent: Sep. 12, 2023

(54) CHROMIUM-CATALYZED PRODUCTION OF ALCOHOLS FROM HYDROCARBONS

(71) Applicant: Chevron Phillips Chemical Company LP, The Woodlands, TX (US)

(72) Inventors: Carlos A. Cruz, Kingwood, TX (US); Masud M. Monwar, Bartlesville, OK (US); Max P. McDaniel, Bartlesville, OK (US); Jared Barr, Bartlesville, OK (US); Kathy S. Clear, Bartlesville, OK (US); William C. Ellis, Bartlesville, OK (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 17/867,782

(22) Filed: Jul. 19, 2022

(65) Prior Publication Data

US 2022/0348527 A1 Nov. 3, 2022

Related U.S. Application Data

(60) Division of application No. 17/501,020, filed on Oct. 14, 2021, now Pat. No. 11,440,865, which is a continuation of application No. 17/019,428, filed on Sep. 14, 2020, now Pat. No. 11,180,435.

(60) Provisional application No. 62/900,687, filed on Sep. 16, 2019.

(51) Int. Cl.

| | | |
|---|---|---|
| *B01J 21/06* | (2006.01) |
| *B01J 21/08* | (2006.01) |
| *B01J 23/26* | (2006.01) |
| *B01J 38/02* | (2006.01) |
| *B01J 37/08* | (2006.01) |
| *B01J 37/34* | (2006.01) |
| *C07C 29/72* | (2006.01) |
| *C07C 29/50* | (2006.01) |
| *C07C 37/58* | (2006.01) |
| *C07C 45/33* | (2006.01) |
| *C07C 31/20* | (2006.01) |
| *C07C 29/48* | (2006.01) |
| *C07C 29/09* | (2006.01) |
| *C07C 51/215* | (2006.01) |
| *C07C 31/04* | (2006.01) |
| *B01J 35/02* | (2006.01) |
| *B01J 35/10* | (2006.01) |
| *C07C 29/17* | (2006.01) |
| *C07C 45/29* | (2006.01) |

(52) U.S. Cl.
CPC ............ *C07C 29/72* (2013.01); *B01J 21/063* (2013.01); *B01J 21/08* (2013.01); *B01J 23/26* (2013.01); *B01J 37/08* (2013.01); *B01J 37/34* (2013.01); *B01J 37/345* (2013.01); *B01J 38/02* (2013.01); *C07C 29/09* (2013.01); *C07C 29/48* (2013.01); *C07C 29/50* (2013.01); *C07C 31/20* (2013.01); *C07C 37/58* (2013.01); *C07C 45/33* (2013.01); *C07C 51/215* (2013.01); *B01J 35/023* (2013.01); *B01J 35/1019* (2013.01); *B01J 35/1023* (2013.01); *B01J 35/1042* (2013.01); *C07C 29/17* (2013.01); *C07C 31/04* (2013.01); *C07C 45/292* (2013.01)

(58) Field of Classification Search
CPC . B01J 21/063; B01J 21/08; B01J 23/26; B01J 35/023; B01J 35/1019; B01J 35/1023; B01J 35/1042; B01J 38/02; C07C 29/50; C07C 37/58; C07C 45/33; C01C 51/215
See application file for complete search history.

(56) References Cited

U.S. PATENT DOCUMENTS

| | | |
|---|---|---|
| 2,857,442 A | 10/1958 | Hay |
| 3,166,537 A | 1/1965 | Gregg |
| 3,201,476 A | 8/1965 | Baker |
| 3,242,099 A | 3/1966 | Manyik |
| 3,245,179 A | 4/1966 | Hawkins |
| 3,694,422 A | 9/1972 | Long |
| 3,857,901 A | 12/1974 | Dowden |

(Continued)

FOREIGN PATENT DOCUMENTS

| | | |
|---|---|---|
| CN | 1150766 C | 5/2004 |
| CN | 101264953 B | 8/2010 |

(Continued)

OTHER PUBLICATIONS

McDaniel et al., Journal of Catalysis, (1983), v.82, p. 98-109.*

(Continued)

*Primary Examiner* — Yong L Chu
(74) *Attorney, Agent, or Firm* — Merchant & Gould P.C.

(57) ABSTRACT

Processes for converting a hydrocarbon reactant into an alcohol compound and/or a carbonyl compound are disclosed, and these processes include the steps of forming a supported chromium catalyst comprising chromium in a hexavalent oxidation state, irradiating the hydrocarbon reactant and the supported chromium catalyst with a light beam at a wavelength in the UV-visible spectrum to reduce at least a portion of the supported chromium catalyst to form a reduced chromium catalyst, and hydrolyzing the reduced chromium catalyst to form a reaction product comprising the alcohol compound and/or the carbonyl compound. The supported chromium catalyst can be formed by heat treating a supported chromium precursor, contacting a chromium precursor with a solid support while heat treating, or heat treating a solid support and then contacting a chromium precursor with the solid support.

23 Claims, No Drawings

(56) References Cited

U.S. PATENT DOCUMENTS

| | | | |
|---|---|---|---|
| 3,887,494 A | 6/1975 | Dietz | |
| 4,248,735 A | 2/1981 | McDaniel | |
| 4,393,253 A | 7/1983 | Michaelson | |
| 4,460,756 A | 7/1984 | McDaniel | |
| 4,501,885 A | 2/1985 | Sherk | |
| 4,588,790 A | 5/1986 | Jenkins, III | |
| 4,794,096 A | 12/1988 | Ewen | |
| 4,808,561 A | 2/1989 | Welborn, Jr. | |
| 5,220,080 A * | 6/1993 | Lyons | C07C 29/50 |
| | | | 568/910.5 |
| 5,352,749 A | 10/1994 | Dechellis | |
| 5,436,304 A | 7/1995 | Griffin | |
| 5,565,175 A | 10/1996 | Hottovy | |
| 5,575,979 A | 11/1996 | Hanson | |
| 5,576,259 A | 11/1996 | Hasegawa | |
| 5,635,438 A | 6/1997 | Cowfer | |
| 5,641,842 A | 6/1997 | McDaniel | |
| 5,739,220 A | 4/1998 | Shamshoum | |
| 5,807,938 A | 9/1998 | Kaneko | |
| 5,919,983 A | 7/1999 | Rosen | |
| 5,955,557 A | 9/1999 | Machida | |
| 6,239,235 B1 | 5/2001 | Hottovy | |
| 6,262,191 B1 | 7/2001 | Hottovy | |
| 6,310,167 B1 | 10/2001 | Kanzawa | |
| 6,380,444 B1 | 4/2002 | Bjerrum | |
| 6,518,375 B1 | 2/2003 | Monoi | |
| 6,825,377 B1 | 11/2004 | Beller | |
| 6,833,415 B2 | 12/2004 | Kendrick | |
| 7,112,643 B2 | 9/2006 | McDaniel | |
| 7,238,756 B2 | 7/2007 | Ehrman | |
| 7,294,599 B2 | 11/2007 | Jensen | |
| 7,304,199 B2 | 12/2007 | Xu | |
| 7,326,760 B2 | 2/2008 | Cann | |
| 7,407,591 B2 | 8/2008 | De Battisti | |
| 7,531,606 B2 | 5/2009 | Hendrickson | |
| 7,598,327 B2 | 10/2009 | Shaw | |
| 7,601,665 B2 | 10/2009 | McDaniel | |
| 7,648,940 B2 | 1/2010 | Holtcamp | |
| 7,649,062 B2 | 1/2010 | Matsunaga | |
| 7,884,163 B2 | 2/2011 | McDaniel | |
| 7,956,138 B2 | 6/2011 | Holtcamp | |
| 8,114,353 B2 | 2/2012 | Benham | |
| 8,114,946 B2 | 2/2012 | Yang | |
| 8,309,485 B2 | 11/2012 | Yang | |
| 8,623,973 B1 | 1/2014 | McDaniel | |
| 8,703,886 B1 | 4/2014 | Yang | |
| 8,822,608 B1 | 9/2014 | Bhandarkar | |
| 8,969,228 B2 | 3/2015 | Nazarpoor | |
| 9,006,367 B2 | 4/2015 | McDaniel | |
| 9,023,959 B2 | 5/2015 | McDaniel | |
| 9,096,699 B2 | 8/2015 | McDaniel | |
| 9,169,337 B2 | 10/2015 | Rohatgi | |
| 9,273,170 B2 | 3/2016 | Hlavinka | |
| 9,346,897 B2 | 5/2016 | Cui | |
| 9,394,393 B2 | 7/2016 | Hlavinka | |
| 9,758,599 B2 | 9/2017 | Ding | |
| 9,796,798 B2 | 10/2017 | Praetorius | |
| 9,802,841 B2 | 10/2017 | Maruo | |
| 9,988,468 B2 | 6/2018 | McDaniel | |
| 10,000,594 B2 | 6/2018 | Hlavinka | |
| 10,213,766 B2 | 2/2019 | Praetorius | |
| 10,246,528 B2 | 4/2019 | McDaniel | |
| 10,287,369 B2 | 5/2019 | Schwerdtfeger | |
| 10,358,506 B2 | 7/2019 | Ding | |
| 10,435,527 B2 | 10/2019 | Praetorius | |
| 10,442,881 B2 | 10/2019 | Hlavinka | |
| 10,654,953 B2 | 5/2020 | McDaniel | |
| 10,835,890 B2 | 11/2020 | Cann | |
| 10,858,459 B2 | 12/2020 | McDaniel | |
| 11,180,435 B2 | 11/2021 | Cruz | |
| 2004/0059070 A1 | 3/2004 | Whitte | |
| 2007/0219085 A1 | 9/2007 | De Battisti | |
| 2008/0032886 A1 | 2/2008 | Yeh | |
| 2013/0206453 A1 | 8/2013 | Fagrell | |
| 2014/0221692 A1 | 8/2014 | Netemeyer | |
| 2015/0191554 A1 | 7/2015 | McDaniel | |
| 2017/0073439 A1 | 3/2017 | Ewart | |
| 2017/0274356 A1 | 9/2017 | Cann | |
| 2018/0079845 A1 | 3/2018 | Doufas | |
| 2019/0153129 A1 | 5/2019 | McDaniel | |
| 2019/0184389 A1 | 6/2019 | Neygandhi | |
| 2019/0308172 A1 | 10/2019 | Zou | |
| 2020/0086307 A1 | 3/2020 | Monwar | |
| 2020/0087430 A1 | 3/2020 | Clear | |
| 2020/0239605 A1 | 7/2020 | McDaniel | |
| 2021/0077981 A1 | 3/2021 | Cruz | |
| 2021/0078920 A1 | 3/2021 | Cruz | |
| 2021/0078926 A1 | 3/2021 | Barr | |
| 2021/0078927 A1 | 3/2021 | McDaniel | |
| 2022/0081370 A1 | 3/2022 | Monwar | |

FOREIGN PATENT DOCUMENTS

| | | |
|---|---|---|
| CN | 108203476 A | 6/2018 |
| CN | 106317267 B | 12/2018 |
| CN | 104774280 B | 9/2019 |
| CN | 106893015 B | 9/2019 |
| CN | 108439533 B | 7/2020 |
| CN | 107311263 B | 11/2020 |
| CN | 107108800 B | 3/2021 |
| JP | H05310601 A | 11/1993 |
| JP | 2010132597 A | 6/2010 |
| JP | 2012101986 A | 5/2012 |
| WO | 2018125690 A1 | 7/2018 |
| WO | 2020060888 A2 | 3/2020 |
| WO | 2020060889 A2 | 3/2020 |
| WO | 2021055270 A1 | 3/2021 |
| WO | 2021055271 A1 | 3/2021 |
| WO | 2021055272 A1 | 3/2021 |

OTHER PUBLICATIONS

Economy et al., Journal of Catalysis, (1965), v.4, p. 446-453.*
International Search Report and Written Opinion, PCT/US2020/050655, dated Dec. 3, 2020, 16 pages.
Awasthy, A.K. and Jan Rocek, "The Nature of the Transition State in the Oxidation of Olefins by Chromium (VI)," JACS 91;4, Feb. 12, 1969, pp. 991-996.
Baker, L. M., et al., Oxidation of olefins by supported chromium oxide, The Journal of Organic Chemistry, vol. 33, No. 2, pp. 616-618 (Year: 1968).
Barzan, et al., Ligands Make the Difference: Molecular Insights into CrVI/SiO2 Phillips Catalyst during Ethylene Polymerization, J. Am. Chem. Soc., 2017, 139, 47, 17064-17073.
Brown, et al., "Mechanism of Initiation in the Phillips Ethylene Polymerization Catalyst: Redox Processes Leading to the Active Site", ACS Catal. 2015, 5, 5574-5583.
Cainelli, et. al., "Reactivity and Structure Concepts in Organic Chemistry", vol. 19, "Chromium Oxidations in Organic Chemistry", Springer Verlag Berlin 1984, p. 8.
Chakrabarti, et al., "Operando Molecular Spectroscopy During Ethylene Polymerization by Supported CrOx/SiO2 Catalysts: Active Sites, Reaction Intermediates, and Structure-Activity Relationship", Top. Catal. 2016, 59 p. 725-739.
Cruz, et al., "Identification of the Starting Group on the Initial PE Chain Produced by Phillips Catalyst", Macromolecules 2019, 52, 5750-5760.
Economy, et.al., "Supported Barium Chromate—A New Oxidation Catalyst", J. Catalysis, vol. 4, No. 4, Aug. 1, 1965, pp. 446-453.
Fendrick, et al., "Actinacyclobutanes. Implementation of Thermochemically Based Strategies for the Ring-Opening Stoichiometric C—H Functionalization of Saturated and Olefinic Hydrocarbons", J. Am. Chem. Soc. 1986,108, 425-437.
Finch, "Reduction Studies on Supported Chromic Anhydride Catalysts," Journal of Catalysis, 43, 1976, pp. 111-121.
Floryan, et al., Strain Effect and Dual Initiation Pathway in Cr(III)/SiO2 Polymerization Catalysts from Amorphous Periodic Models, J. Catalysis 2017, 346, 50-56.
Gierada, et. al., "Active sites formation and their transformations during ethylene polymerization by the Phillips CrOx/SiO2 catalyst", J. Catal., 2017, 352, 314-328.

(56) References Cited

OTHER PUBLICATIONS

Groppo, et al., "The Structure of Active Centers and the Ethylene Polymerization Mechanism on the Cr/SiO2 Catalyst: A Frontier for the Characterization Method", Chem. Rev. 2005, 105, 115-183.
International Search Report and Written Opinion, PCT/US2020/050650, dated Dec. 2, 2020, 14 pages.
International Search Report and Written Opinion, PCT/US2020/050657, dated Dec. 21, 2020, 15 pages.
Joseph, et al., "Products of the Initial Reduction of the Phillips Catalyst by Olefins", Journal of Catalysis 377 (2019) 550-564.
Kissin, et al., "Chemistry of Olefin Polymerization Reactions with Chromium-Based Catalysts", Journal of Polymer Science: Part A: Polymer Chemistry, 2008, 46, 5330-5347.
Kohler, et al., "Infrared Spectroscopic Characterization of Chromium Carbonyl Species Formed by Ultraviolet Photoreduction of Silica-Supported Chromium(VI) in Carbon Monoxide," J. Phys. Chem. 1994, 98, pp. 4336-4342.
McDaniel, et al., "The Activation Of The Phillips Polymerization Catalyst; I. Influence Of The Hydroxyl Population", J. Catalysis, vol. 82, No. 1, Jul. 1, 1983, pp. 98-109.
Milas, N.A., The hydroxylation of unsaturated substances. III. The use of vanadium pentoxide and chromium trioxide as Catalysts of hydroxylation, The Journal of the American Chemical Society, vol. 59, No. 11, pp. 2342-2344 (Year: 1937).
Milas, N.A. et al., The hydroxylation of unsaturated substances. IV. The catalytic hydroxylation of unsaturated hydrocarbons, The Journal of the American Chemical Society, vol. 59, No. 11, pp. 2345-2347 (Year: 1937).
Mino, et al., "Photoinduced Ethylene Polymerization on the CrVI/SiO2 Phillips Catalyst," J. Phys. Chem. C 2019, 123, 13 pp. 8145-8152.
Monwar, et.al., "Ethylene polymerization by hydrocarbon-reduced Cr/silica catalyst", Journal of Catalysis 394 (2021) 451-464.
Potter, et al., "Reduction of the Phillips Catalyst by Various Olefins: Stoichiometry, Thermochemistry, Reaction Products and Polymerization Activity", J. Catal. 344 (2016) 657-668.
Schwerdtfeger, E., et al., Reduction of Cr(VI) polymerization catalysts by non-olefinic hydrocarbons, Applied Catalysis A: General, 423-424, pp. 91-99 (Year: 2012).
Scott, et al. "Surface Organometallic Investigation of the Mechanism of Ethylene Polymerization by Silica-Supported Cr Catalysts", J. Chem. Eng. Sci. 2001, 56, 4155-4163.
Thompson, et al. "'Sigma-Bond metathesis' for carbon-hydrogen bonds of hydrocarbons and Sc—R (R = H, alkyl, aryl) bonds of permethylscandocene derivatives. Evidence for noninvolvement of the pi system in electrophilic activation of aromatic and vinylic C—H bonds", J. Am. Chem. Soc. 1987, 109, 203-219.
Weckhuysen et al., "Alkane dehydrogenation over supported chromium oxide catalysts," Catalysis Today 51 (1999) pp. 223-232.
Welch, et al., "The Activation Of The Phillips Polymerization Catalyst; II. Activation By Reduction-Reoxidation", J Catalysis, vol. 82, No. 1, Jul. 1, 1983, pp. 110-117.
Wikipedia, Ultraviolet, Oct. 2019, p. 1-17 (Year: 2019).
Zhu, et al., "Synthesis and Structural Characterization of M(PMe3)3(O2CR)2(OH2)H2 (M) Mo, W): Aqua-Hydride Complexes of Molybdenum and Tungsten", Inorg. Chem. 2005, 44, 9637-9639.
Form PTO-892 issued in corresponding U.S. Appl. No. 17/470,066 mailed on Apr. 6, 2023, 1 pp.
Search Report issued in related Chinese Application No. 2019800569668, dated Nov. 3, 2022, 4 pp.
Office Action issued by European Patent Office dated Feb. 28, 2023 for application No. 19783394.0. 6 pages.

\* cited by examiner

US 11,753,358 B2

CHROMIUM-CATALYZED PRODUCTION OF ALCOHOLS FROM HYDROCARBONS

REFERENCE TO RELATED APPLICATION

This application is a divisional application of U.S. patent application Ser. No. 17/501,020, filed on Oct. 14, 2021, now U.S. Pat. No. 11,440,865, which is a continuation application of U.S. patent application Ser. No. 17/019,428, filed on Sep. 14, 2020, now U.S. Pat. No. 11,180,435, which claims the benefit of U.S. Provisional Patent Application No. 62/900,687, filed on Sep. 16, 2019, the disclosures of which are incorporated herein by reference in their entirety.

FIELD OF THE INVENTION

The present disclosure generally relates to methods for converting hydrocarbons into alcohols and/or carbonyls, and more particularly, relates to performing such methods with a supported chromium catalyst.

BACKGROUND OF THE INVENTION

Alcohol compounds can be prepared by various synthesis techniques from alkanes, but such techniques often require halogens or harsh reaction conditions. Alternative reaction schemes are therefore desirable. Accordingly, it is to these ends that the present invention is generally directed.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

Aspects of this invention are directed to processes for converting a hydrocarbon reactant into an alcohol compound and/or a carbonyl compound, and such processes can comprise (a)(i) heat treating a supported chromium precursor at a peak temperature from about 50° C. to about 1000° C. to form a supported chromium catalyst comprising chromium in a hexavalent oxidation state, or (a)(ii) contacting a chromium precursor with a solid support while heat treating at a peak temperature from about 50° C. to about 1000° C. to form a supported chromium catalyst comprising chromium in a hexavalent oxidation state, or (a)(iii) heat treating a solid support at a peak temperature from about 50° C. to about 1000° C. and then contacting a chromium precursor with the solid support to form a supported chromium catalyst comprising chromium in a hexavalent oxidation state, (b) irradiating the hydrocarbon reactant and the supported chromium catalyst with a light beam at a wavelength in the UV-visible spectrum to reduce at least a portion of the supported chromium catalyst to form a reduced chromium catalyst, and (c) hydrolyzing the reduced chromium catalyst to form a reaction product comprising the alcohol compound and/or the carbonyl compound. Optionally, these processes can further comprise a step of calcining all or a portion of the reduced chromium catalyst to regenerate the supported chromium catalyst.

In step (b), at least a portion of the chromium on the reduced chromium catalyst can have at least one bonding site with a hydrocarboxy group (a —O-hydrocarbon group), which upon hydrolysis in step (c), can release an alcohol compound and/or carbonyl compound analog of the hydrocarbon compound. For instance, if the hydrocarbon is cyclohexane (or methane), then the alcohol compound can be cyclohexanol (or methanol).

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects may be directed to various feature combinations and sub-combinations described in the detailed description.

Definitions

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter are described such that, within particular aspects, a combination of different features can be envisioned. For each and every aspect and each and every feature disclosed herein, all combinations that do not detrimentally affect the catalysts, compositions, processes, or methods described herein are contemplated with or without explicit description of the particular combination. Additionally, unless explicitly recited otherwise, any aspect or feature disclosed herein can be combined to describe inventive catalysts, compositions, processes, or methods consistent with the present disclosure.

Generally, groups of elements are indicated using the numbering scheme indicated in the version of the periodic table of elements published in *Chemical and Engineering News*, 63(5), 27, 1985. In some instances, a group of elements can be indicated using a common name assigned to the group; for example, alkali metals for Group 1 elements, alkaline earth metals for Group 2 elements, transition metals for Group 3-12 elements, and halogens or halides for Group 17 elements.

The term "hydrocarbon" whenever used in this specification and claims refers to a compound containing only carbon and hydrogen, whether saturated or unsaturated. Other identifiers can be utilized to indicate the presence of particular groups in the hydrocarbon (e.g., halogenated hydrocarbon indicates the presence of one or more halogen atoms replacing an equivalent number of hydrogen atoms in the hydrocarbon). Non-limiting examples of hydrocarbons include alkanes (linear, branched, and cyclic), alkenes (olefins), and aromatics, among other compounds. Herein, cyclics and aromatics encompass fused ring compounds such as bicyclics and polycyclics.

For any particular compound or group disclosed herein, any name or structure (general or specific) presented is intended to encompass all conformational isomers, regioisomers, stereoisomers, and mixtures thereof that can arise from a particular set of substituents, unless otherwise specified. The name or structure (general or specific) also encompasses all enantiomers, diastereomers, and other optical isomers (if there are any) whether in enantiomeric or racemic forms, as well as mixtures of stereoisomers, as would be recognized by a skilled artisan, unless otherwise specified. For instance, a general reference to pentane includes n-pentane, 2-methyl-butane, and 2,2-dimethylpropane; and a general reference to a butyl group includes a n-butyl group, a sec-butyl group, an iso-butyl group, and a t-butyl group.

Unless otherwise specified, the term "substituted" when used to describe a group, for example, when referring to a substituted analog of a particular group, is intended to describe any non-hydrogen moiety that formally replaces a hydrogen in that group, and is intended to be non-limiting. Also, unless otherwise specified, a group or groups can also be referred to herein as "unsubstituted" or by equivalent terms such as "non-substituted," which refers to the original group in which a non-hydrogen moiety does not replace a hydrogen within that group. Moreover, unless otherwise specified, "substituted" is intended to be non-limiting and include inorganic substituents or organic substituents as understood by one of ordinary skill in the art.

The terms "contacting" and "combining" are used herein to describe catalysts, compositions, processes, and methods in which the materials or components are contacted or combined together in any order, in any manner, and for any length of time, unless otherwise specified. For example, the materials or components can be blended, mixed, slurried, dissolved, reacted, treated, impregnated, compounded, or otherwise contacted or combined in some other manner or by any suitable method or technique.

"BET surface area" as used herein means the surface area as determined by the nitrogen adsorption Brunauer, Emmett, and Teller (BET) method according to ASTM D1993-91, and as described, for example, in Brunauer, S., Emmett, P. H., and Teller, E., "Adsorption of gases in multimolecular layers," J. Am. Chem. Soc., 60, 3, pp. 309-319, the contents of which are expressly incorporated by reference herein.

In this disclosure, while catalysts, compositions, processes, and methods are described in terms of "comprising" various components or steps, the catalysts, compositions, processes, and methods also can "consist essentially of" or "consist of" the various components or steps, unless stated otherwise.

The terms "a," "an," and "the" are intended to include plural alternatives, e.g., at least one. For instance, the disclosure of "a hydrocarbon reactant," "a solid oxide," etc., is meant to encompass one, or mixtures or combinations of more than one, hydrocarbon reactant, solid oxide, etc., unless otherwise specified.

Several types of ranges are disclosed in the present invention. When a range of any type is disclosed or claimed, the intent is to disclose or claim individually each possible number that such a range could reasonably encompass, including end points of the range as well as any sub-ranges and combinations of sub-ranges encompassed therein. For example, when a chemical compound having a certain number of carbon atoms is disclosed or claimed, the intent is to disclose or claim individually every possible number that such a range could encompass, consistent with the disclosure herein. For example, the disclosure that a hydrocarbon reactant contains a $C_1$ to $C_{18}$ alkane compound, or in alternative language, an alkane compound having from 1 to 18 carbon atoms, as used herein, refers to a compound that can have 1, 2, 3, 4, 5, 6, 7, 8, 9, 10, 11, 12, 13, 14, 15, 16, 17, or 18 carbon atoms, as well as any range between these two numbers (for example, a $C_1$ to $C_8$ alkane compound), and also including any combination of ranges between these two numbers (for example, a $C_2$ to $C_4$ alkane compound and a $C_{12}$ to $C_{16}$ alkane compound).

Similarly, another representative example follows for the amount of chromium on the supported chromium catalyst consistent with aspects of this invention. By a disclosure that the amount of chromium can be in a range from about 0.1 to about 15 wt. %, the intent is to recite that the amount of chromium can be any amount in the range and, for example, can be equal to about 0.1, about 0.2, about 0.3, about 0.4, about 0.5, about 0.6, about 0.7, about 0.8, about 0.9, about 1, about 2, about 3, about 4, about 5, about 6, about 7, about 8, about 9, about 10, about 11, about 12, about 13, about 14, or about 15 wt. %. Additionally, the amount of chromium can be within any range from about 0.1 to about 15 wt. % (for example, from about 0.1 to about 5 wt. %), and this also includes any combination of ranges between about 0.1 and about 15 wt. % (for example, the amount of chromium can be in a range from about 0.5 to about 2.5 wt. %, or from about 5 to about 15 wt. %). Further, in all instances, where "about" a particular value is disclosed, then that value itself is disclosed. Thus, the disclosure that the amount of chromium can be from about 0.1 to about 15 wt. % also discloses an amount of chromium from 0.1 to 15 wt. % (for example, from 0.1 to 5 wt. %) and this also includes any combination of ranges between 0.1 and 15 wt. % (for example, the amount of chromium can be in a range from 0.5 to 2.5 wt. %, or from 5 to 15 wt. %). Likewise, all other ranges disclosed herein should be interpreted in a manner similar to these examples.

The term "about" means that amounts, sizes, formulations, parameters, and other quantities and characteristics are not and need not be exact, but can be approximate including being larger or smaller, as desired, reflecting tolerances, conversion factors, rounding off, measurement errors, and the like, and other factors known to those of skill in the art. In general, an amount, size, formulation, parameter or other quantity or characteristic is "about" or "approximate" whether or not expressly stated to be such. The term "about" also encompasses amounts that differ due to different equilibrium conditions for a composition resulting from a particular initial mixture. Whether or not modified by the term "about," the claims include equivalents to the quantities. The term "about" can mean within 10% of the reported numerical value, and often within 5% of the reported numerical value.

Although any methods, devices, and materials similar or equivalent to those described herein can be used in the practice or testing of the invention, the typical methods, devices, and materials are herein described.

All publications and patents mentioned herein are incorporated herein by reference for the purpose of describing and disclosing, for example, the constructs and methodologies that are described in the publications, which might be used in connection with the presently described invention.

DETAILED DESCRIPTION OF THE INVENTION

The present invention is generally directed to the conversion of a hydrocarbon into an analogous alcohol compound and/or carbonyl compound. Unexpectedly, it was found that the combined use of a supported chromium catalyst, light reduction, and hydrolysis can efficiently convert the hydrocarbon (e.g., an alkane) into the analogous alcohol compound and/or carbonyl compound, and beneficially, even at ambient temperature.

Unexpectedly, it was also found that the high calcination/activation temperatures that are generally required for supported chromium polymerization catalysts—such as 600-

900° C.—are not necessary to produce alcohols and/or carbonyls as described herein. Whereas calcination below these traditional high temperatures results in a poor or inactive supported chromium polymerization catalyst, heat treatment temperatures in the 100-500° C. range were effective to remove free water and/or dry the supported catalyst and/or convert or stabilize the chromium (VI), thereby efficiently producing desirable alcohol and/or carbonyl products.

Also unexpectedly, chromate compounds—such as potassium chromate, potassium dichromate, and the like—which are completely ineffective for use in polymerization catalysts, were very efficient catalysts for converting hydrocarbons into alcohols and/or carbonyls. And beneficially, very low heat treatment temperatures can be used, since chromium (VI) is already present.

Generally, supported chromium polymerization catalysts are limited to loadings of chromium of about 1 wt. %. When the chromium (VI) is stabilized by binding to the silica or other support, the loading cannot be too high, or the chromium can degrade into unusable chromium (III). However, and beneficially, high chromium loadings of 5-10 wt. %, and even 20-50 wt. %, can easily be utilized in the process described herein, and these higher loadings result in higher overall yields of the alcohol and/or carbonyl products (more chromium equals more product). Conversely, it was also found that low chromium loadings, such as less than 0.5 wt. %, can be highly selective to desirable alcohol and/or carbonyl products, although they are not very active for polymerization.

Processes for Converting Hydrocarbons into Alcohols

Disclosed herein are processes for converting a hydrocarbon reactant into an alcohol compound and/or a carbonyl compound. These processes can comprise (a)(i) heat treating a supported chromium precursor at a peak temperature from about 50° C. to about 1000° C. to form a supported chromium catalyst comprising chromium in a hexavalent oxidation state, or (a)(ii) contacting a chromium precursor with a solid support while heat treating at a peak temperature from about 50° C. to about 1000° C. to form a supported chromium catalyst comprising chromium in a hexavalent oxidation state, or (a)(iii) heat treating a solid support at a peak temperature from about 50° C. to about 1000° C. and then contacting a chromium precursor with the solid support to form a supported chromium catalyst comprising chromium in a hexavalent oxidation state, (b) irradiating the hydrocarbon reactant and the supported chromium catalyst with a light beam at a wavelength in the UV-visible spectrum to reduce at least a portion of the supported chromium catalyst to form a reduced chromium catalyst, and (c) hydrolyzing the reduced chromium catalyst to form a reaction product comprising the alcohol compound and/or the carbonyl compound. While not wishing to be bound by theory, it is believed that in step (b), at least a portion of the chromium on the reduced chromium catalyst can have at least one bonding site with a hydrocarboxy group (a —O-hydrocarbon group) such as an alkoxy group, which upon hydrolysis in step (c), can release an alcohol compound and/or carbonyl compound analog of the hydrocarbon compound. The reduced chromium catalyst has an average oxidation state less than that of the supported chromium catalyst.

Generally, the features of this process (e.g., the chromium precursor, the supported chromium precursor, the peak temperature, the hydrocarbon reactant, the supported chromium catalyst, the reduced chromium catalyst, the light beam, and the conditions under which the irradiating step and the hydrolyzing step are conducted, among others) are independently described herein and these features can be combined in any combination to further describe the disclosed processes to produce alcohol compounds and/or carbonyl compounds. Moreover, additional process steps can be performed before, during, and/or after any of the steps in any of the processes disclosed herein, and can be utilized without limitation and in any combination to further describe these processes, unless stated otherwise. Further, any alcohol compounds and/or carbonyl compounds produced in accordance with the disclosed processes are within the scope of this disclosure and are encompassed herein.

Referring first to step (a)(i), a supported chromium precursor can be heat treated at a peak temperature from about 50° C. to about 1000° C. to form the supported chromium catalyst comprising chromium in a hexavalent oxidation state. The supported chromium precursor can be prepared by contacting a solid support with a chromium precursor (a chromium source) prior to heat treating. Generally, the chromium precursor can comprise $CrO_3$ or anything calcinable to $CrO_3$. Typical chromium precursors, therefore, can include chromium (III) acetate, basic chromium (III) acetate, chromium (III) nitrate, chromium (III) sulfate, chromium (III) chloride (or bromide or iodide), chromium (II) chloride (or bromide or iodide), chromium (III) malate (or propionate, or gluconate, or citrate). These chromium precursors, beneficially, are soluble in water. Other organic chromium compounds can be used as the chromium precursor, and these can be used with an alcohol or other organic solvent, including chromium (III) naphthenate, chromium (III) acetylacetonate and other diketonates, chromyl chloride, chromium (III) alkoxides (e.g., methoxide or ethoxide), and higher carboxylates such as chromium (III) 2-ethyl hexanoate or chromium (III) propionate. Organic chromium (0) compounds also can be used in a hydrocarbon solvent, such as diarene chromium (0) compounds like bis-cumene chromium (0), bis-benzene chromium (0), bis-toluene chromium (0), and so forth. Similarly, bis-cyclopentadienyl chromium (II), bis-indenyl chromium (II), and other cyclopentadienyl derivatives can be used as the chromium precursor, as well as chromium (0) hexacarbonyl. Further, sodium, potassium, or ammonium chromate or dichromate can likewise be used as the chromium source.

Thus, when the process comprises step (a)(i), the supported chromium precursor can comprise $CrO_3$ (or anything calcinable to $CrO_3$), chromium (III) acetate, basic chromium (III) acetate, chromium (III) nitrate, chromium (III) sulfate, chromium (III) chloride (or bromide or iodide), chromium (II) chloride (or bromide or iodide), chromium (III) malate (or propionate, gluconate, or citrate), chromium (III) naphthenate, chromium (III) acetylacetonate (or other diketonate), chromyl chloride, chromium (III) methoxide (or ethoxide or other alkoxide), chromium (III) 2-ethyl hexanoate (or propionate or other carboxylate), a chromium (0) compound (e.g., chromium (0) hexacarbonyl, or a diarene chromium (0) compound such as bis-cumene chromium (0), bis-benzene chromium (0), or bis-toluene chromium (0)), a chromium (II) cyclopentadienyl-type compound (e.g., bis-cyclopentadienyl chromium (II) or bis-indenyl chromium (II)), a chromate compound (e.g., potassium chromate, sodium chromate, ammonium chromate, potassium dichromate, sodium dichromate, or ammonium dichromate), and the like, as well as any combination thereof. In a particular aspect, the supported chromium precursor can comprise potassium chromate, sodium chromate, ammonium chromate, potassium dichromate, sodium dichromate, ammonium dichromate, or any combination thereof.

In step (a)(ii), the chromium precursor can be contacted with a solid support while heat treating at a peak temperature from about 50° C. to about 1000° C. to form the supported chromium catalyst comprising chromium in a hexavalent oxidation state. Certain chromium precursors are volatile and can be added during the heat treatment. For example, chromium (III) acetylacetonate sublimes above about 100° C., so it can be dry-mixed with the solid support and the mixture heat treated. The chromium vaporizes during the heating step and reacts with the support to form chromium (VI). Chromium (0) hexacarbonyl is another example of this approach. Alternatively, chromyl chloride is a liquid that evaporates easily. Thus, in one aspect, chromyl chloride can be vaporized into a gas stream used to fluidize the solid support during heat treatment. It passes up through the solid support bed as a vapor, and is adsorbed onto and/or reacts with the solid support. It was found that chromium (VI) on these catalysts tends to be mobile on the support, passing easily from one particle to another during heat treatment, and therefore in another aspect, the support can be dry-mixed with a non-volatile chromium precursor, such as chromic oxide ($Cr_2O_3$) followed by the heat treatment. The $Cr_2O_3$ particles are oxidized on the surface to chromium (VI) which then contact the support, and pass over onto the support. Many other chromium precursors can be used in this way, such as for example, $CrO_3$, chromium (III) sulfate, chromium (III) nitrate, and the like. Other examples include sodium, potassium, or ammonium chromate or dichromate, which is unexpected, because such alkali metal chromates are not usually acceptable for use in polymerization catalysts because of low activity and sintering of the solid support.

Thus, when the process comprises step (a)(ii), the chromium precursor can comprise chromium (III) acetylacetonate, chromium (0), chromyl chloride, chromic oxide ($Cr_2O_3$), $CrO_3$, chromium (III) sulfate, chromium (III) nitrate, a chromate compound (e.g., potassium chromate, sodium chromate, ammonium chromate, potassium dichromate, sodium dichromate, or ammonium dichromate), and the like, as well as any combination thereof. In a particular aspect, the chromium precursor can comprise potassium chromate, sodium chromate, ammonium chromate, potassium dichromate, sodium dichromate, ammonium dichromate, or any combination thereof.

In step (a)(iii), a solid support can be heat treated at a peak temperature from about 50° C. to about 1000° C. and then contacted with a chromium precursor to form the supported chromium catalyst comprising chromium in a hexavalent oxidation state. Chromium (VI) can be added after the heat treatment. For example, after the solid support is heat treated, it can be impregnated with an anhydrous, non-protic chromium (VI) solution, followed by evaporation of the solvent. It is typically important for the solvent be non-protic, so as to not re-hydrate the support. Examples of this approach include dissolving $CrO_3$ in acetonitrile and impregnating the heat-treated support with this solution, followed by evaporation of the solvent. Organic chromium (VI) esters also can be dissolved in hydrocarbons and impregnated onto the heat-treated support. Examples include bis(t-butyl) chromate dissolved in hexane, or bis(triphenylsilyl)chromate dissolved in toluene. Chromyl chloride is another precursor that can be dissolved in hydrocarbon solvents or acetonitrile, or even used through vapor phase contact with the support after the heat-treatment. Sodium, potassium, or ammonium chromate or dichromate can be dissolved in acetonitrile, or even in a hydrocarbon (e.g., a crown-ether may be used to improve the solubility) and utilized as the chromium precursor.

Thus, when the process comprises step (a)(iii), the chromium precursor can comprise $CrO_3$, bis(t-butyl) chromate (or bis(triphenylsilyl) chromate, or other organic chromium (VI) ester), chromyl chloride, an inorganic chromate compound (e.g., potassium chromate, sodium chromate, ammonium chromate, potassium dichromate, sodium dichromate, or ammonium dichromate), and the like, as well as any combination thereof. The solvent can be removed, in whole or in part, prior to the irradiating step. Alternatively, if the solvent is the desired hydrocarbon reactant, it is not necessary to remove prior to irradiating the hydrocarbon reactant and the supported chromium catalyst.

Step (a) can be conducted at a variety of temperature and time conditions, as would be recognized by a skilled artisan, and can be generally selected to convert all or a portion of the chromium to hexavalent chromium. Depending upon whether step (a)(i) or (a)(ii) or (a)(iii) is used and the particular chromium precursor (e.g., a chromium (III) precursor or a chromate/dichromate compound), the peak temperature in step (a)(i) and (a)(ii) and (a)(iii) can encompass a broad range. Representative ranges for the peak temperature include from about 300° C. to about 1000° C., from about 400° C. to about 870° C., from about 300° C. to about 600° C., from about 100° C. to about 500° C., from about 50° C. to about 400° C., from about 100° C. to about 300° C., from about 50° C. to about 200° C., and the like. These temperature ranges also are meant to encompass circumstances where the heat treatment is performed at a series of different temperatures, instead of at a single fixed temperature, falling within the respective temperature ranges, wherein at least one temperature is within the recited ranges.

Depending upon the temperature, the heat treatment step can function as predominately a drying step (e.g., 50-300° C.) or predominantly a calcining step (e.g., 500-850° C.). In an aspect, a chromium precursor or a supported chromium precursor in a low oxidation state typically will necessitate a higher temperature and oxidizing atmosphere to convert the chromium into hexavalent chromium. In contrast, in another aspect, a chromium precursor or a supported chromium precursor that is already in the hexavalent state (e.g., chromate or dichromate) may only need a low heat treatment temperature to dry or remove excess water/moisture prior to exposing the supported chromium catalyst to light irradiation. Consequently, in this latter aspect, an oxidizing atmosphere may not be necessary.

Likewise, depending upon some of these same factors, step (a)(i) and (a)(ii) and (a)(iii) can be conducted in an oxidizing atmosphere in some aspects, while step (a)(i) and (a)(ii) and (a)(iii) can be conducted in an inert atmosphere in other aspects.

A variety of hydrocarbon reactants can be used in the process to form an alcohol compound and/or a carbonyl compound, inclusive of saturated aliphatic hydrocarbon compounds, unsaturated aliphatic hydrocarbon compounds, linear aliphatic hydrocarbon compounds, branched aliphatic hydrocarbon compounds, and cyclic aliphatic hydrocarbon compounds, as well as combinations thereof. Thus, the hydrocarbon reactant can comprise a linear alkane compound, a branched alkane compound, a cyclic alkane compound, or a combination thereof. Additionally or alternatively, the hydrocarbon reactant can comprise an aromatic compound, such as benzene, toluene, and the like, as well as substituted versions thereof, and including combinations thereof.

Any suitable carbon number hydrocarbon can be used, such that the hydrocarbon reactant can comprise a $C_n$ hydrocarbon compound (and the alcohol compound often can comprise a $C_n$ alcohol compound, and the carbonyl compound often can comprise a $C_n$ carbonyl compound). While not being limited thereto, the integer n can range from 1 to 36 in one aspect, from 1 to 18 in another aspect, from 1 to 12 in yet another aspect, and from 1 to 8 in still another aspect.

Therefore, the hydrocarbon reactant can comprise any suitable carbon number alkane compound, for instance, a $C_1$ to $C_{36}$ alkane compound; alternatively, a $C_1$ to $C_{18}$ alkane compound; alternatively, a $C_1$ to $C_{12}$ alkane compound; or alternatively, a $C_1$ to $C_8$ alkane compound. If desired, the hydrocarbon reactant can contain a single alkane compound of relatively high purity, such as at least about 90 wt. % of a single alkane compound, at least about 95 wt. % of a single alkane compound, at least about 98 wt. % of a single alkane compound, or at least about 99 wt. % of a single alkane compound, and so forth. Alternatively, the hydrocarbon reactant can comprise a mixture of two or more hydrocarbon reactants, such as two or more alkane compounds in any relative proportions. Thus, the hydrocarbon reactant can comprise a mixture of $C_1$ to $C_{18}$ alkane compounds, a mixture of $C_1$ to $C_4$ alkane compounds, a mixture of $C_2$ to $C_6$ alkane compounds, a mixture of $C_6$ to $C_8$ alkane compounds, or a mixture of $C_{10}$ to $C_{14}$ alkane compounds, and the like.

Similarly, the hydrocarbon reactant can comprise any suitable carbon number olefin compound, for instance, a $C_2$ to $C_{36}$ olefin compound; alternatively, a $C_2$ to $C_{18}$ olefin compound; alternatively, a $C_2$ to $C_{12}$ olefin compound; or alternatively, a $C_2$ to $C_8$ olefin compound. As above, if desired, the hydrocarbon reactant can contain a single olefin compound of relatively high purity, such as at least about 90 wt. % of a single olefin compound, at least about 95 wt. % of a single olefin compound, at least about 98 wt. % of a single olefin compound, or at least about 99 wt. % of a single olefin compound, and so forth. Alternatively, the hydrocarbon reactant can comprise a mixture of two or more hydrocarbon reactants, such as two or more olefin compounds in any relative proportions. Thus, the hydrocarbon reactant can comprise a mixture of $C_2$ to $C_{36}$ olefin compounds, a mixture of $C_2$ to $C_{18}$ olefin compounds, a mixture of $C_2$ to $C_{12}$ olefin compounds, or a mixture of $C_2$ to $C_8$ olefin compounds, and the like.

Likewise, the hydrocarbon reactant can comprise any suitable carbon number aromatic compound, for instance, a $C_6$ to $C_{36}$ aromatic compound; alternatively, a $C_6$ to $C_{18}$ aromatic compound; alternatively, a $C_6$ to $C_{12}$ aromatic compound; or alternatively, a $C_6$ to $C_8$ aromatic compound. As above, if desired, the hydrocarbon reactant can contain a single aromatic compound of relatively high purity, such as at least about 90 wt. % of a single aromatic compound, at least about 95 wt. % of a single aromatic compound, at least about 98 wt. % of a single aromatic compound, or at least about 99 wt. % of a single aromatic compound, and so forth. Alternatively, the hydrocarbon reactant can comprise a mixture of two or more hydrocarbon reactants, such as two or more aromatic compounds in any relative proportions. Thus, the hydrocarbon reactant can comprise a mixture of $C_6$ to $C_{36}$ aromatic compounds, a mixture of $C_6$ to $C_{18}$ aromatic compounds, a mixture of $C_6$ to $C_{12}$ aromatic compounds, or a mixture of $C_6$ to $C_8$ aromatic compounds, and the like.

Illustrative examples of alkane, olefin, and aromatic hydrocarbon reactants can include methane, ethane, propane, butane (e.g., n-butane or isobutane), pentane (e.g., n-pentane, neopentane, or isopentane), hexane, heptane, octane, nonane, decane, undecane, dodecane, tridecane, tetradecane, pentadecane, hexadecane, heptadecane, octadecane, ethylene, propylene, 1-butene, 1-pentene, 1-hexene, 1-heptene, 1-octene, 1-decene, 1-dodecene, 1-tetradecene, 1-hexadecene, 1-octadecene, cyclopentene, cyclohexene, benzene, toluene, ethylbenzene, xylene, mesitylene, and the like, as well as combinations thereof.

Thus, the hydrocarbon reactant can comprise a mixture of an aliphatic hydrocarbon and an aromatic hydrocarbon. In a non-limiting aspect, the hydrocarbon reactant can comprise methane; alternatively, ethane; alternatively, propane; alternatively, butane; alternatively, pentane; alternatively, hexane; alternatively, heptane; alternatively, octane; alternatively, nonane; alternatively, decane; alternatively, undecane; alternatively, dodecane; alternatively, tridecane; alternatively, tetradecane; alternatively, pentadecane; alternatively, hexadecane; alternatively, heptadecane; alternatively, octadecane; alternatively, ethylene; alternatively, propylene; alternatively, 1-butene; alternatively, 1-pentene; alternatively, 1-hexene; alternatively, 1-heptene; alternatively, 1-octene; alternatively, 1-decene; alternatively, 1-dodecene; alternatively, 1-tetradecene; alternatively, 1-hexadecene; alternatively, 1-octadecene; alternatively, cyclopentene; alternatively, cyclohexene; alternatively, benzene; alternatively, toluene; alternatively, ethylbenzene; alternatively, xylene; or alternatively, mesitylene.

In an aspect, the hydrocarbon (alkane) reactant can comprise methane, ethane, propane, n-butane, isobutane, n-pentane, neopentane, isopentane, n-hexane, n-heptane, n-octane, n-decane, n-dodecane, and the like, or any combination thereof, while in another aspect, the hydrocarbon (alkane) reactant can comprise methane, ethane, propane, butane, pentane, hexane, and the like, or any combination thereof. In yet another aspect, the hydrocarbon (olefin) reactant can comprise ethylene, propylene, 1-butene, 1-pentene, 1-hexene, 1-heptene, 1-octene, 1-decene, 1-dodecene, 1-tetradecene, 1-hexadecene, 1-octadecene, cyclopentene, cyclohexene, and the like, or any combination thereof, or alternatively, ethylene, propylene, 1-butene, 1-pentene, 1-hexene, 1-heptene, 1-octene, or any combination thereof. In still another aspect, the hydrocarbon (aromatic) reactant can comprise benzene, toluene, ethylbenzene, xylene, mesitylene, and the like, or any combination thereof.

Generally, the irradiating step can be performed under any conditions sufficient to accommodate the irradiation of the hydrocarbon reactant and the supported chromium catalyst (comprising chromium in a hexavalent oxidation state) with a light beam and to form the reduced chromium catalyst (having a lower oxidation state). The irradiation step can comprise reducing at least a portion of the hexavalent chromium species to a reduced oxidation state—for instance, Cr (II) and/or Cr (III) and/or Cr (IV) and/or Cr (V) species, any of which may be present on the reduced chromium catalyst.

The relative amount (or concentration) of the hydrocarbon reactant to the amount of chromium (in the supported chromium catalyst) can alter the efficacy of the reduction process. In certain aspects, the molar ratio of the hydrocarbon reactant to the chromium (in the supported chromium catalyst) can be at least about 0.25:1, at least about 0.5:1, at least about 1:1, at least about 10:1, at least about 100:1, at least about 1000:1, or at least about 10,000:1. Thus, a large excess of the hydrocarbon reactant can be used, and there is no particular limit as to the maximum amount of hydrocarbon reactant.

The temperature and pressure of the irradiating step can be such that the hydrocarbon reactant remains a liquid throughout reduction of the supported chromium catalyst in one aspect, and the hydrocarbon remains a gas throughout reduction of the supported chromium catalyst in another aspect. Advantageously, it was found that reducing supported chromium compounds at lower temperatures than those typically required to reduce hexavalent chromium species using heat and not light, was possible by the irradiating steps disclosed herein. In certain aspects, the irradiating step can be conducted at a temperature of less than about 200° C., less than about 100° C., less than about 70° C., less than about 40° C., from about 0° C. to about 200° C., from about −100° C. to about 100° C., from about 0° C. to about 100° C., or from about 10° C. to about 40° C., and can produce a reduced chromium catalyst (e.g., with at least a portion of the chromium on the reduced chromium catalyst having at least one bonding site with a hydrocarboxy group). These temperature ranges also are meant to encompass circumstances where the irradiation is performed at a series of different temperatures, instead of at a single fixed temperature, falling within the respective temperature ranges, wherein at least one temperature is within the recited ranges.

The irradiating step can be further characterized by an amount of time that the hydrocarbon reactant and supported chromium catalyst are exposed to the light beam, e.g., an exposure time. Without being bound by theory, it is believed that exposure to the light beam in the presence of the hydrocarbon reactant is responsible for the reduction of the supported chromium catalyst, and therefore it follows that the exposure time must be sufficient to allow this transformation to occur, whether the transformation occurs very rapidly or very slowly. Thus, in certain aspects, and not being limited thereto, the exposure time can be in a range from about 15 sec to about 48 hr, from about 15 sec to about 24 hr, from about 1 hr to about 8 hr, from about 15 min to about 4 hr, from about 1 min to about 6 hr, from about 5 min to about 1 hr, from about 10 min to about 2 hr, from about 1 min to about 1 hr, or from about 1 min to about 15 min. As one of skill in the art would recognize, the exposure time can vary based on the intensity of the light beam, the wavelength(s) of the light beam, and so forth. Agitation, mixing, or other suitable technique can be used to ensure that the mixture of the supported chromium catalyst (e.g., particles) and the hydrocarbon reactant is uniformly exposed to the light beam irradiation.

The supported chromium catalyst and the hydrocarbon reactant can be continuously subjected to irradiation (for the entirety of the exposure time), or the irradiation can be pulsed (such that the total of the pulses equates to the exposure time, e.g., sixty 1-sec pulses equates to a 60-sec exposure time). Combinations of periods of continuous irradiation and pulsed irradiation can be utilized, if desired.

In the disclosed processes, irradiation of a supported chromium catalyst with a light beam in the UV-visible spectrum, in the presence of a hydrocarbon reactant, results in a chromium catalyst with a reduced oxidation state (e.g., a reduced chromium catalyst). A wide range of wavelengths, light sources, and intensities can be used, as long as these wavelengths, light sources, and intensities are sufficient to reduce at least a portion of the hexavalent chromium species present in the supported chromium catalyst. In certain aspects, for instance, the light can be derived from any suitable source, such as from sunlight, a fluorescent white light, an LED diode, and/or a UV lamp. The distance from non-sunlight sources can be varied as needed (e.g., minimized) to increase the effectiveness of the irradiation.

The wavelength of the light can be any in the range of UV-visible light. In certain aspects, the wavelength of the light beam can be a single wavelength, or more than one wavelength, such as a range of wavelengths. For instance, the wavelength of the light beam can be a range of wavelengths spanning at least 25 nm, at least 50 nm, at least 100 nm, at least 200 nm, or at least 300 nm. In one aspect, the wavelength of the light beam can comprise a single wavelength or a range of wavelengths in the UV spectrum, in the visible spectrum (from 380 nm to 780 nm), or both. In another aspect, the wavelength of the light beam can comprise a single wavelength or a range of wavelengths in the 200 nm to 750 nm range. Yet, in another aspect, the wavelength of the light beam can comprise a single wavelength or a range of wavelengths in the 300 to 750 nm range, the 350 nm to 650 nm range, the 300 nm to 600 nm range, the 300 nm to 500 nm range, or the 400 nm to 500 nm range. In other aspects, the wavelength of the light beam can comprise a single wavelength or a range of wavelengths below 600 nm, below 525 nm, or below 500 nm; additionally or alternatively, above 300 nm, above 350 nm, above 400 nm, or above 450 nm.

The light beam of the irradiating step also can be characterized by its intensity (e.g., the total amount of light emitted from a source). In certain aspects, the light beam can have an intensity of at least about 500 lumens, at least about 1,000 lumens, at least about 2,000 lumens at least about 5,000 lumens, at least about 10,000 lumens, at least about 20,000 lumens, at least about 50,000 lumens, or at least about 100,000 lumens. Thus, there may not be an upper limit on the intensity of the light source. Alternatively, the light beam can have an intensity in a range from about 50 to about 50,000 lumens, from about 50 to about 10,000 lumens, from about 100 to about 5,000 lumens, or from about 500 to about 2,000 lumens. Additionally, the light beam can be characterized by the amount of light reaching the hydrocarbon reactant and supported chromium catalyst, i.e., the flux. In certain aspects, the hydrocarbon reactant and the supported chromium catalyst comprising chromium in a hexavalent oxidation state can be irradiated by at least about 100 lux, at least about 500 lux, at least about 1000 lux, at least about 2000 lux, at least about 5000 lux, at least about 10,000 lux, at least about 20,000 lux, at least about 100,000 lux, or in a range from about 10,000 to about 1,000,000 lux, from about 50,000 to about 500,000 lux, or from about 50,000 to about 200,000 lux. Additionally or alternatively, in certain aspects, the hydrocarbon reactant and the supported chromium catalyst comprising chromium in the hexavalent oxidation state can be irradiated with a light beam having a power of at least about 50 watts, at least about 100 watts, at least about 200 watts, at least about 500 watts, at least about 1,000 watts, or at least about 2,000 watts.

Any suitable reactor or vessel can be used to form the alcohol compound and/or the carbonyl compound, non-limiting examples of which can include a flow reactor, a continuous reactor, a packed bed reactor, a fluidized bed reactor, and a stirred tank reactor, including more than one reactor in series or in parallel, and including any combination of reactor types and arrangements.

In one aspect, the hydrocarbon reactant can be in a gas phase during the irradiating step. In another aspect, the hydrocarbon reactant can be in a liquid phase during the irradiating step. In another aspect, the disclosed processes can comprise irradiating a slurry (e.g., a loop slurry) of the solid supported chromium catalyst in the hydrocarbon reactant. In yet another aspect, the disclosed processes can comprise contacting the hydrocarbon reactant with a fluidized bed of the solid supported chromium catalyst, and irradiating while contacting (fluidizing). In still another aspect, the disclosed processes can comprise contacting the hydrocarbon reactant (e.g., in the gas phase or in the liquid phase) with a fixed bed of the solid supported chromium catalyst, and irradiating while contacting. As a skilled artisan would recognize, there are other methods for contacting the hydrocarbon reactant and the solid supported chromium catalysts and irradiating, and the disclosed processes are not limited solely to those disclosed herein. For instance, the hydrocarbon reactant and the supported chromium catalyst can be mixed or contacted in a stirred tank, and irradiated while being mixed in the stirred tank.

Any suitable pressure can be used to contact the hydrocarbon reactant and the supported catalyst and to form the reduced chromium catalyst, and such can depend upon the carbon number of the hydrocarbon reactant (and its boiling point), the type of reactor configuration and desired mode for contacting the hydrocarbon reactant with the (solid) supported chromium catalyst, among other considerations.

Often, the process for forming the reduced chromium catalyst (and subsequently, the alcohol and/or carbonyl compound) can be a flow process and/or a continuous process. In such circumstances, the hydrocarbon reactant-supported chromium catalyst contact time (or reaction time) can be expressed in terms of weight hourly space velocity (WHSV)—the ratio of the weight of the hydrocarbon reactant which comes in contact with a given weight of the supported chromium catalyst per unit time (units of g/g/hr, or $hr^{-1}$).

While not limited thereto, the WHSV employed for the disclosed processes can have a minimum value of 0.01 $hr^{-1}$, 0.02 $hr^{-1}$, 0.05 $hr^{-1}$, 0.1 $hr^{-1}$, 0.25 $hr^{-1}$, or 0.5 $hr^{-1}$; or alternatively, a maximum value of 500 $hr^{-1}$, 400 $hr^{-1}$, 300 $hr^{-1}$, 100 $hr^{-1}$, 50 $hr^{-1}$, 10 $hr^{-1}$, 5 $hr^{-1}$, 2 $hr^{-1}$, or 1 $hr^{-1}$. Generally, the WHSV can be in a range from any minimum WHSV disclosed herein to any maximum WHSV disclosed herein. In a non-limiting aspect, the WHSV can be in a range from about 0.01 $hr^{-1}$ to about 500 $hr^{-1}$; alternatively, from about 0.01 $hr^{-1}$ to about 10 $hr^{-1}$; alternatively, from about 0.01 $hr^{-1}$ to about 1 $hr^{-1}$; alternatively, from about 0.02 $hr^{-1}$ to about 400 $hr^{-1}$; alternatively, from about 0.02 $hr^{-1}$ to about 50 $hr^{-1}$; alternatively, from about 0.05 $hr^{-1}$ to about 300 $hr^{-1}$; alternatively, from about 0.05 $hr^{-1}$ to about 5 $hr^{-1}$; alternatively, from about 0.1 $hr^{-1}$ to about 400 $hr^{-1}$; alternatively, from about 0.25 $hr^{-1}$ to about 50 $hr^{-1}$; alternatively, from about 0.25 $hr^{-1}$ to about 2 $hr^{-1}$; alternatively, from about 0.5 $hr^{-1}$ to about 400 $hr^{-1}$; alternatively, from about 0.5 $hr^{-1}$ to about 5 $hr^{-1}$; or alternatively, from about 0.5 $hr^{-1}$ to about 2 $hr^{-1}$. Other WHSV ranges are readily apparent from this disclosure.

Referring now to the hydrolyzing step, in which the reduced chromium catalyst (e.g., with at least a portion of the chromium on the reduced chromium catalyst having at least one bonding site with a hydrocarboxy group) is hydrolyzed to form a reaction product comprising the alcohol compound and/or the carbonyl compound. Generally, the temperature, pressure, and time features of the hydrolyzing step can be the same as those disclosed herein for the irradiating step, although not limited thereto. For example, the hydrolyzing step can be conducted at a temperature of less than about 200° C., less than about 100° C., less than about 70° C., less than about 40° C., from about 0° C. to about 200° C., from about 0° C. to about 100° C., or from about 10° C. to about 40° C., and can result in the formation of a reaction product containing the alcohol compound and/or the carbonyl compound. These temperature ranges also are meant to encompass circumstances where the hydrolyzing step is performed at a series of different temperatures, instead of at a single fixed temperature, falling within the respective temperature ranges, wherein at least one temperature is within the recited ranges.

While not limited thereto, the hydrolyzing step can comprise contacting the reduced chromium catalyst with a hydrolysis agent. Illustrative and non-limiting examples of suitable hydrolysis agents can include water, steam, an alcohol agent, an acid agent, an alkaline agent, and the like, as well as combinations thereof. Thus, mixtures of water and various alcohol agents, such as $C_1$-$C_4$ alcohols (and/or acid agents, such as hydrochloric acid, sulfuric acid, acetic acid, ascorbic acid, and the like; and/or alkaline agents, such as sodium hydroxide, ammonium hydroxide, and the like) in any relative proportions can be used as the hydrolysis agent. Thus, the pH of the hydrolysis agent(s) can range from acid to neutral to basic pH values, generally encompassing a pH range from about 1 (or less) to about 13-13.5.

Optionally, the hydrolysis agent can further comprise any suitable reducing agent, and representative reducing agents include ascorbic acid, iron (II) reducing agents, zinc reducing agents, and the like, as well as combinations thereof. These are sometimes useful for preventing unwanted secondary oxidations by unreacted chromium (VI). Further, they also can be used to tailor the product range by increasing selectivity. For example, in some aspects, adding reducing agents to the hydrolysis agent can eliminate all carbonyl products and instead produce only alcohol products.

As disclosed herein, the reaction product can comprise an alcohol compound and/or a carbonyl compound, which can be an analog of the hydrocarbon reactant. Thus, typical alcohol compounds that can be synthesized using the processes disclosed herein can include, for instance, methanol, ethanol, isopropanol, butanols, pentanols, hexanols, heptanols, octanols, nonanols, decanols, undecanols, dodecanols, tridecanols, tetradecanols, pentadecanols, hexadecanols, heptadecanols, octadecanols, benzyl alcohol, phenols, xylenols, and the like, as well as combinations thereof. Herein, an alcohol compound encompasses mono-alcohol compounds as well as diol compounds (e.g., ethanediol and hexanediols).

In addition to or in lieu of the alcohol compound, the reaction product can comprise a carbonyl compound, such as an aldehyde compound, a ketone compound, or an organic acid compound, as well as any combination of aldehyde, ketone, and organic acid compounds. Thus, enols are encompassed herein, since the reaction product can comprise an alcohol compound, a carbonyl compound, or both. In some aspects, the alcohol or carbonyl product can contain unsaturation. For example, the carbon(s) adjacent to the alcohol or carbonyl group can contain a double bond. While not wishing to be bound by theory, it is believed that the allyl C—H bond is particularly susceptible to being attacked by the chromium (VI). Thus, when the reductant hydrocarbon has a double bond, a typical alcohol product, and often among the most abundant, contains the —OH group on the adjacent allyl carbon.

The processes described herein result in an unexpectedly high conversion of the hydrocarbon reactant and/or yield to the alcohol compound (or carbonyl compound). In one aspect, the minimum conversion (or yield) can be at least about 2 wt. %, at least about 5 wt. %, at least about 10 wt. %, at least about 15 wt. %, or at least about 25 wt. %. Additionally, the maximum conversion (or yield) can be about 50 wt. %, about 70 wt. %, about 80 wt. %, about 90 wt. %, about 95 wt. %, or about 99 wt. %, and can approach 100% conversion of the hydrocarbon reactant (or yield of the alcohol compound, or yield of the carbonyl compound). Generally, the conversion (or yield) can be in a range from any minimum conversion (or yield) disclosed herein to any maximum conversion (or yield) disclosed herein. Non-limiting ranges of conversion (or yield) can include from about 5 wt. % to about 99 wt. %, from about 10 wt. % to about 95 wt. %, or from about 15 wt. % to about 70 wt. %. For conversion, the percentages are the amount of the hydrocarbon reactant converted based on the initial amount of the hydrocarbon reactant. The yield values are weight percentages, and are based on the weight of the alcohol compound (or carbonyl compound) produced to the weight of hydrocarbon reactant. In some aspects, these conversions (or yields) can be achieved in a batch process, while in other aspects, these conversions (or yields) can be achieved in a flow or continuous process, such as, for example, a single pass or multiple passes through a reactor (e.g., a fixed bed reactor). Often, the conversion and yield can be manipulated by varying the ratio of reductant hydrocarbon feed to the amount of chromium (VI), and by varying other reaction conditions such as time, temperature, and irradiation.

Also unexpectedly, continuous flow processes for producing the alcohol compound and/or carbonyl compound in accordance with this invention have unexpectedly high single pass conversions of the hydrocarbon reactant (or single pass yields to the desired alcohol or carbonyl compound). In one aspect, the minimum single pass conversion (or yield) can be at least about 2 wt. %, at least about 5 wt. %, at least about 10 wt. %, at least about 15 wt. %, or at least about 25 wt. %. Additionally, the maximum single pass conversion (or yield) can be about 50 wt. %, about 70 wt. %, about 80 wt. %, about 90 wt. %, about 95 wt. %, or about 99 wt. %, and can approach 100% conversion of the hydrocarbon reactant (or yield of the alcohol compound, or yield of the carbonyl compound), depending upon the reaction conditions. Generally, the single pass conversion (or yield) can be in a range from any minimum single pass conversion (or yield) disclosed herein to any maximum single pass conversion (or yield) disclosed herein. Non-limiting ranges of single pass conversion (or yield) can include from about 5 wt. % to about 99 wt. %, from about 10 wt. % to about 95 wt. %, or from about 15 wt. % to about 70 wt. %.

The yield of the alcohol compound (or carbonyl compound) also can be characterized based on the amount of chromium (VI) (of the supported chromium catalyst). For instance, the molar ratio (molar yield) of the alcohol compound (or carbonyl compound) based on the moles of chromium (VI) can be at least about 0.01 moles, at least about 0.02 moles, at least about 0.05 moles, at least about 0.1 moles, or at least about 0.25 moles (and up to 2 moles, up to about 1.8 moles, up to about 1.6 moles, up to about 1.4 moles, up to about 1.2 moles, or up to about 1 mole) of the alcohol compound (or carbonyl compound) per mole of chromium (VI). If more than one alcohol compound and/or carbonyl compound is/are produced, then this ratio represents the total moles of alcohol and/or carbonyl compounds produced per mole of chromium (VI).

The processes to produce the alcohol compounds and/or carbonyl compounds disclosed herein typically can result in—after hydrolysis—a crude reaction mixture containing residual hydrocarbon reactant (e.g., methane), a desired alcohol compound and/or carbonyl compound (e.g., methanol), and by-products. In many instances, it can be desirable to isolate or separate at least a portion (and in some cases, all) of the hydrocarbon reactant from the reaction product after step (c). This can be accomplished using any suitable technique, which can include but is not limited to, extraction, filtration, evaporation, or distillation, as well as combinations of two or more of these techniques. In particular aspects of this invention, the isolating or separating step utilizes distillation at any suitable pressure (one or more than one distillation column can be used).

Additionally or alternatively, the processes disclosed herein can further comprise a step of separating at least a portion (and in some cases, all) of the alcohol compound (or carbonyl compound) from the reaction product, and any suitable technique can be used, such as extraction, filtration, evaporation, distillation, or any combination thereof. Additionally or alternatively, the processes disclosed herein can further comprise a step of separating at least a portion (and in some cases, all) of the reduced chromium catalyst from the reaction product after step (c), and as above, any suitable technique(s) can be used.

Optionally, certain components of the reaction product—such as the hydrocarbon reactant—can be recovered and recycled to the reactor. In such instances, at least a portion (and in some cases, all) of the hydrocarbon reactant can be recycled and contacted with supported chromium catalyst again, such that the overall conversion of the hydrocarbon product is increased after multiple contacts with the supported chromium catalyst (or multiple passes through the reactor containing the supported chromium catalyst).

If desired, the processes disclosed herein can further comprise a step of (d) calcining at least a portion (and in some cases, all) of the reduced chromium catalyst to regenerate the supported chromium catalyst. Any suitable calcining conditions can be used, for instance, subjecting the reduced chromium catalyst to an oxidizing atmosphere at any suitable calcining temperature and time conditions, such as a calcining temperature from about 300° C. to about 1000° C., from about 500° C. to about 900° C., or from about 550° C. to about 870° C., for a time period of from about 1 min to about 24 hr, from about 1 hr to about 12 hr, or from about 30 min to about 8 hr.

The calcining step can be conducted using any suitable technique and equipment, whether batch or continuous. For instance, the calcining step can be performed in a belt calciner or, alternatively, a rotary calciner. In some aspects, the calcining step can be performed in a batch or continuous calcination vessel comprising a fluidized bed. As would be recognized by those of skill in the art, other suitable techniques and equipment can be employed for the calcining step, and such techniques and equipment are encompassed herein.

An illustrative and non-limiting example of the processes disclosed herein follows for the case in which a $C_1$-$C_6$ alkane is the hydrocarbon reactant, and a $C_1$-$C_6$ alcohol is the alcohol product. In this case, the process for converting a $C_1$-$C_6$ alkane into a $C_1$-$C_6$ alcohol can comprise (a)(i) heat treating a supported chromium precursor at a peak temperature from about 50° C. to about 1000° C. to form a supported chromium catalyst comprising chromium in a hexavalent oxidation state, or (a)(ii) contacting a chromium precursor with a solid support while heat treating at a peak temperature from about 50° C. to about 1000° C. to form a supported chromium catalyst comprising chromium in a hexavalent oxidation state, or (a)(iii) heat treating a solid support at a peak temperature from about 50° C. to about 1000° C. and then contacting a chromium precursor with the solid support to form a supported chromium catalyst comprising chromium in a hexavalent oxidation state, (b) irradiating the $C_1$-$C_6$ alkane and the supported chromium catalyst with a light beam at a wavelength in the UV-visible spectrum to reduce at least a portion of the supported chromium catalyst to form a reduced chromium catalyst, and (c) hydrolyzing the reduced chromium catalyst (with any suitable hydrolysis agent) to form a reaction product comprising the $C_1$-$C_6$ alcohol.

The $C_1$-$C_6$ alkane can comprise methane (or ethane, or propane, or butane, or pentane, or hexane) and the $C_1$-$C_6$ alcohol can comprise methanol (or ethanol, or propanol, or butanol, or pentanol, or hexanol). The reaction product can, in some aspects, further comprise an organic acid compound. For instance, when the reactant comprises methane, the reaction product can comprise methanol, and in some aspects, can further comprise formic acid. Moreover, as discussed herein, the process to convert a $C_1$-$C_6$ alkane into a $C_1$-$C_6$ alcohol optionally can further comprise a step of (d) calcining at least a portion (and in some cases, all) of the reduced chromium catalyst to regenerate the supported chromium catalyst.

The $C_1$-$C_6$ alkane can comprise methane (or ethane, or propane, or butane, or pentane, or hexane, or cyclopentane, or cyclohexane) and the $C_1$-$C_6$ alcohol can comprise methanol (or ethanol, or propanols, or butanols, or pentanols, or hexanols, or cyclopentanol, or cyclohexanol). The reaction product can, in some aspects, further comprise an organic acid compound. For instance, when the reactant comprises methane, the reaction product can comprise methanol, and in some aspects, can further comprise formic acid. When the reactant is ethane or ethylene, the reaction product can comprise methanol, ethanol, formic acid and/or acetic acid. Moreover, as discussed herein, the process to convert a $C_1$-$C_6$ alkane into a $C_1$-$C_6$ alcohol optionally can further comprise a step of (d) calcining at least a portion (and in some cases, all) of the reduced chromium catalyst to regenerate the supported chromium catalyst.

Chromium Catalysts

Various solid supports can be used for the supported chromium precursor, the supported chromium catalyst, and the reduced chromium catalyst, such as conventional solid oxides and zeolites. Generally, the solid oxide can comprise oxygen and one or more elements selected from Group 2, 3, 4, 5, 6, 7, 8, 9, 10, 11, 12, 13, 14, or 15 of the periodic table, or comprise oxygen and one or more elements selected from the lanthanide or actinide elements (See: Hawley's Condensed Chemical Dictionary, 11$^{th}$ Ed., John Wiley & Sons, 1995; Cotton, F. A., Wilkinson, G., Murillo, C. A., and Bochmann, M., Advanced Inorganic Chemistry, 6$^{th}$ Ed., Wiley-Interscience, 1999). For example, the solid oxide can comprise oxygen and an element, or elements, selected from Al, B, Be, Bi, Cd, Co, Cr, Cu, Fe, Ga, La, Mn, Mo, Ni, Sb, Si, Sn, Sr, Th, Ti, V, W, P, Y, Zn, and Zr. Illustrative examples of solid oxide materials or compounds that can be used as solid support can include, but are not limited to, $Al_2O_3$, $B_2O_3$, BeO, $Bi_2O_3$, CdO, $CO_3O_4$, $Cr_2O_3$, CuO, $Fe_2O_3$, $Ga_2O_3$, $La_2O_3$, $Mn_2O_3$, $MoO_3$, NiO, $P_2O_5$, $Sb_2O_5$, $SiO_2$, $SnO_2$, SrO, $ThO_2$, $TiO_2$, $V_2O_5$, $WO_3$, $Y_2O_3$, ZnO, $ZrO_2$, and the like, including mixed oxides thereof, and combinations thereof.

The solid oxide can encompass oxide materials such as silica, "mixed oxide" compounds thereof such as silica-titania, and combinations or mixtures of more than one solid oxide material. Mixed oxides such as silica-titania can be single or multiple chemical phases with more than one metal combined with oxygen to form the solid oxide. Examples of mixed oxides that can be used as solid oxide include, but are not limited to, silica-alumina, silica-coated alumina, silica-titania, silica-zirconia, alumina-titania, alumina-zirconia, zinc-aluminate, alumina-boria, silica-boria, aluminum phosphate, aluminophosphate, aluminophosphate-silica, titania-zirconia, and the like, or a combination thereof. In some aspects, the solid support can comprise silica, silica-alumina, silica-coated alumina, silica-titania, silica-titania-magnesia, silica-zirconia, silica-magnesia, silica-boria, aluminophosphate-silica, and the like, or any combination thereof. Silica-coated aluminas are encompassed herein; such oxide materials are described in, for example, U.S. Pat. Nos. 7,884,163 and 9,023,959, incorporated herein by reference in their entirety.

The percentage of each oxide in a mixed oxide can vary depending upon the respective oxide materials. As an example, a silica-alumina (or silica-coated alumina) typically has an alumina content from 5 wt. % to 95 wt. %. According to one aspect, the alumina content of the silica-alumina (or silica-coated alumina) can be from 5 wt. % alumina 50 wt. % alumina, or from 8 wt. % to 30 wt. % alumina. In another aspect, high alumina content silica-aluminas (or silica-coated aluminas) can be employed, in which the alumina content of these materials typically ranges from 60 wt. % alumina to 90 wt. % alumina, or from 65 wt. % alumina to 80 wt. % alumina.

In one aspect, the solid oxide can comprise silica-alumina, silica-coated alumina, silica-titania, silica-zirconia, alumina-titania, alumina-zirconia, zinc-aluminate, alumina-boria, silica-boria, aluminum phosphate, aluminophosphate, aluminophosphate-silica, titania-zirconia, or a combination thereof, alternatively, silica-alumina; alternatively, silica-coated alumina; alternatively, silica-titania; alternatively, silica-zirconia; alternatively, alumina-titania; alternatively, alumina-zirconia; alternatively, zinc-aluminate; alternatively, alumina-boria; alternatively, silica-boria; alternatively, aluminum phosphate; alternatively, aluminophosphate; alternatively, aluminophosphate-silica; or alternatively, titania-zirconia.

In another aspect, the solid oxide can comprise silica, alumina, titania, thoria, stania, zirconia, magnesia, boria, zinc oxide, a mixed oxide thereof, or any mixture thereof. In yet another aspect, the solid support can comprise silica, alumina, titania, or a combination thereof; alternatively, silica; alternatively, alumina; alternatively, titania; alternatively, zirconia; alternatively, magnesia; alternatively, boria; or alternatively, zinc oxide. In still another aspect, the solid oxide can comprise silica, alumina, silica-alumina, silica-coated alumina, aluminum phosphate, aluminophosphate, heteropolytungstate, titania, zirconia, magnesia, boria, zinc oxide, silica-titania, silica-yttria, silica-zirconia, alumina-titania, alumina-zirconia, zinc-aluminate, alumina-boria, silica-boria, aluminophosphate-silica, titania-zirconia, and the like, or any combination thereof.

Consistent with certain aspects of this invention, the supported chromium precursor, the supported chromium catalyst, and the reduced chromium catalyst can comprise a chemically-treated solid oxide as the solid support, and where the chemically-treated solid oxide comprises a solid oxide (any solid oxide disclosed herein) treated with an electron-withdrawing anion (any electron withdrawing anion disclosed herein). The electron-withdrawing component used to treat the solid oxide can be any component that increases the Lewis or Brønsted acidity of the solid oxide upon treatment (as compared to the solid oxide that is not treated with at least one electron-withdrawing anion). According to one aspect, the electron-withdrawing component can be an electron-withdrawing anion derived from a salt, an acid, or other compound, such as a volatile organic compound, that serves as a source or precursor for that anion. Examples of electron-withdrawing anions can include, but are not limited to, sulfate, bisulfate, fluoride, chloride, bromide, iodide, fluorosulfate, fluoroborate, phosphate, fluorophosphate, trifluoroacetate, triflate, fluorozirconate, fluorotitanate, phospho-tungstate, tungstate, molybdate, and the like, including mixtures and combinations thereof. In addition, other ionic or non-ionic compounds that serve as sources for these electron-withdrawing anions also can be employed.

It is contemplated that the electron-withdrawing anion can be, or can comprise, fluoride, chloride, bromide, phosphate, triflate, bisulfate, or sulfate, and the like, or any combination thereof, in some aspects provided herein. In other aspects, the electron-withdrawing anion can comprise sulfate, bisulfate, fluoride, chloride, bromide, iodide, fluorosulfate, fluoroborate, phosphate, fluorophosphate, trifluoroacetate, triflate, fluorozirconate, fluorotitanate, and the like, or combinations thereof. Yet, in other aspects, the electron-withdrawing anion can comprise fluoride and/or sulfate.

The chemically-treated solid oxide generally can contain from about 1 wt. % to about 30 wt. % of the electron-withdrawing anion, based on the weight of the chemically-treated solid oxide. In particular aspects provided herein, the chemically-treated solid oxide can contain from about 1 to about 20 wt. %, from about 2 wt. % to about 20 wt. %, from about 3 wt. % to about 20 wt. %, from about 2 wt. % to about 15 wt. %, from about 3 wt. % to about 15 wt. %, from about 3 wt. % to about 12 wt. %, or from about 4 wt. % to about 10 wt. %, of the electron-withdrawing anion, based on the total weight of the chemically-treated solid oxide.

In an aspect, the chemically-treated solid oxide can comprise fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, fluorided-chlorided silica-coated alumina, sulfated silica-coated alumina, phosphated silica-coated alumina, and the like, as well as any mixture or combination thereof.

In another aspect, the chemically-treated solid oxide employed in the supported chromium precursor, the solid support, the supported chromium catalyst, and the reduced chromium catalyst, and the processes described herein can be, or can comprise, a fluorided solid oxide and/or a sulfated solid oxide, non-limiting examples of which can include fluorided alumina, sulfated alumina, fluorided silica-alumina, sulfated silica-alumina, fluorided silica-zirconia, fluorided silica-coated alumina, sulfated silica-coated alumina, and the like, as well as combinations thereof. Additional information on chemically-treated solid oxide can be found in, for instance, U.S. Pat. Nos. 7,294,599, 7,601,665, 7,884, 163, 8,309,485, 8,623,973, and 8,703,886, which are incorporated herein by reference in their entirety.

Representative examples of the supported chromium precursors, supported chromium catalysts, and reduced chromium catalysts (in which a solid oxide is the solid support) include, but are not limited to, chromium/silica, chromium/silica-titania, chromium/silica-titania-magnesia, chromium/silica-alumina, chromium/silica-coated alumina, chromium/aluminophosphate, chromium/alumina, chromium/alumina borate, and the like, or any combination thereof. In one aspect, for instance, the supported chromium precursor, the supported chromium catalyst, and the reduced chromium catalyst can comprise chromium/silica, while in another aspect, the supported chromium precursor, the supported chromium catalyst, and the reduced chromium catalyst can comprise chromium/silica-titania, and in yet another aspect, the supported chromium precursor, the supported chromium catalyst, and the reduced chromium catalyst can comprise chromium/silica-alumina and/or chromium/silica-coated alumina. In circumstances in which the supported chromium precursor, the supported chromium catalyst, and the reduced chromium catalyst comprise chromium/silica-titania, any suitable amount of titanium can be present, including from about 0.1 to about 20 wt. %, from about 0.5 to about 15 wt. %, from about 1 to about 10 wt. %, or from about 1 to about 6 wt. % titanium, based on the total weight of the respective supported chromium precursor, supported chromium catalyst, and reduced chromium catalyst.

Representative examples of supported chromium precursors, supported chromium catalysts, and reduced chromium catalysts (in which a chemically-treated solid oxide is the solid support) include, but are not limited to, chromium/sulfated alumina, chromium/fluorided alumina, chromium/fluorided silica-alumina, chromium/fluorided silica-coated alumina, and the like, as well as combinations thereof.

Consistent with certain aspects of this invention, the supported chromium precursor, the supported chromium catalyst, and the reduced chromium catalyst can comprise a zeolite as the solid support, i.e., a chromium supported zeolite. Any suitable zeolite can be used, for instance, large pore and medium pore zeolites. Large pore zeolites often have average pore diameters in a range of from about 7 Å to about 12 Å, and non-limiting examples of large pore zeolites include L-zeolite, Y-zeolite, mordenite, omega zeolite, beta zeolite, and the like. Medium pore zeolites often have average pore diameters in a range of from about 5 Å to about 7 Å. Combinations of zeolitic supports can be used.

Additional representative examples of zeolites that can be used as solid supports herein include, for instance, a ZSM-5 zeolite, a ZSM-11 zeolite, a EU-1 zeolite, a ZSM-23 zeolite, a ZSM-57 zeolite, an ALPO4-11 zeolite, an ALPO4-41 zeolite, a Ferrierite framework type zeolite, and the like, or any combination thereof.

In the supported chromium precursor, the solid support, the supported chromium catalyst, and the reduced chromium catalyst, the zeolite can be bound with a support matrix (or binder), non-limiting examples of which can include silica, alumina, magnesia, boria, titania, zirconia, various clays, and the like, including mixed oxides thereof, as well as mixtures thereof. For example, the supported chromium precursor, the solid support, the supported chromium catalyst, and the reduced chromium catalyst can comprise a binder comprising alumina, silica, a mixed oxide thereof, or a mixture thereof. The zeolite can be bound with the binder using any method known in the art. While not being limited thereto, the supported chromium precursor, the solid support, the supported chromium catalyst, and the reduced chromium catalyst can comprise a zeolite and from about 3 wt. % to about 35 wt. % binder; alternatively, from about 5 wt. % to about 30 wt. % binder; or alternatively, from about 10 wt. % to about 30 wt. % binder. These weight percentages are based on the total weight of the respective supported chromium precursor, solid support, supported chromium catalyst, and reduced chromium catalyst.

In some aspects herein, the supported chromium precursor, the supported chromium catalyst, and the reduced chromium catalyst can comprise a clay, an activated carbon, or a combination thereof, as the solid support.

It is worth noting that chromium polymerization catalysts usually require chromium loadings in a rather narrow range, typically from 0.5 to 2 wt. %, because higher amounts degrade the polymer and lower amounts result in low activity. However, no such limitation exists in the present invention. Thus, the amount of chromium in the supported chromium catalyst and the reduced chromium catalyst typically can range from about 0.01 to about 50 wt. %; alternatively, from about 0.01 to about 10 wt. %; alternatively, from about 0.1 to about 15 wt. %; alternatively, from about 0.1 to about 0.5 wt. %; alternatively, from about 0.2 to about 10 wt. %; alternatively, from about 0.5 to about 2.5 wt. %; alternatively, from about 2 to about 30 wt. %; or alternatively, from about 3 to about 15 wt. %. These weight percentages are based on the amount of chromium relative to the total weight of the supported chromium catalyst or the reduced chromium catalyst. While not wishing to be bound by theory, it is believed, and the examples below seem to indicate, that lower chromium loadings (e.g., 1 wt. % and less) can result in higher selectivity to a particular alcohol compound (or carbonyl compound), while higher chromium loadings (e.g., 5-15 wt. % and above) can result in higher alcohol and/or carbonyl yields per gram of catalyst.

Likewise, the amount of chromium in an average oxidation state of +5 or less in the reduced chromium catalyst is not particularly limited, and can fall within the same ranges. Thus, the reduced chromium catalyst can contain from about 0.01 to about 50 wt. %, from about 0.01 to about 10 wt. %, from about 0.1 to about 15 wt. %, from about 0.1 to about 0.5 wt. %, from about 0.2 to about 10 wt. %, from about 0.5 to about 2.5 wt. %, from about 2 to about 30 wt. %, or from about 3 to about 15 wt. % of chromium in an average oxidation state of +5 or less, based on the weight of the reduced chromium catalyst.

Generally, at least about 10 wt. % of the chromium in the supported chromium catalyst is present in a hexavalent oxidation state before the reduction step, and more often at least about 20 wt. % is present as chromium (VI). In further aspects, at least about 40 wt. %, at least about 60 wt. %, at least about 80 wt. %, at least about 90 wt. %, or at least about 95 wt. %, of the chromium in the supported chromium catalyst can be present in an oxidation state of +6. These weight percentages are based on the total amount of chromium. Traditional chromium (VI) catalysts often will have an orange, yellow, or tan color, indicating the presence of chromium (VI).

Conversely, less than or equal to about 50 wt. % of the chromium in the reduced chromium catalyst is typically present in an oxidation state of +6 (VI), and more often less than or equal to about 40 wt. %. In further aspects, less than or equal to about 30 wt. %, or less than or equal to about 15 wt. % of chromium in the reduced chromium catalyst can be present in an oxidation state of +6. The minimum amount of chromium (VI) often can be 0 wt. % (no measurable amount), at least about 0.5 wt. %, at least about 1 wt. %, at least about 2 wt. %, or at least about 5 wt. %. These weight percentages are based on the total amount of chromium. The reduced chromium catalysts often will have a green, blue, gray, or black color.

Thus, the irradiation of the supported chromium catalyst—in the presence of the hydrocarbon reactant—ordinarily results in at least about 10 wt. %, at least about 20 wt. %, at least about 40 wt. %, at least about 60 wt. %, at least about 80 wt. %, or at least about 90 wt. %, of the supported chromium catalyst being reduced or converted to form the reduced chromium catalyst.

Additionally or alternatively, the chromium in the reduced chromium catalyst can be characterized by an average valence of less than or equal to about 5.25. More often, the chromium in the reduced chromium catalyst has an average valence of less than or equal to about 5; alternatively, an average valence of less than or equal to about 4.75; alternatively, an average valence of less than or equal to about 4.5; alternatively, an average valence of less than or equal to about 4.25; or alternatively, an average valence of less than or equal to about 4.

It is important to note that chromium polymerization catalysts require supports of high porosity so as to allow fragmentation of the catalyst and subsequent egress of the polymer chains, which are hundreds of times longer than the pore diameter in the catalyst. However, in the present invention, no such restriction exists. Thus, the total pore volume of the supported chromium precursor, the solid support, the supported chromium catalyst, and the reduced chromium catalyst is not particularly limited. For instance, the supported chromium precursor, the solid support, the supported chromium catalyst, and the reduced chromium catalyst can have a total pore volume in a range from about 0.1 to about 5 mL/g, from about 0.15 to about 5 mL/g, from about 0.1 to about 3 mL/g, from about 0.5 to about 2.5 mL/g, or from about 0.1 to about 0.8 mL/g. Likewise, the surface area of the supported chromium precursor, the solid support, the supported chromium catalyst, and the reduced chromium catalyst is not limited to any particular range. Generally, however, the supported chromium precursor, the solid support, the supported chromium catalyst, and the reduced chromium catalyst can have a BET surface area in a range from about 50 to about 2000 $m^2/g$, from about 50 to about 700 $m^2/g$, from about 50 to about 400 $m^2/g$, from about 600 to about 1200 $m^2/g$, from about 150 to about 525 $m^2/g$, or from about 200 to about 400 $m^2/g$.

The supported chromium precursor, the solid support, the supported chromium catalyst, and the reduced chromium catalyst can have any suitable shape or form, and such can depend on the type of process that is employed to convert the hydrocarbon reactant into the alcohol compound and/or carbonyl compound (e.g., fixed bed versus fluidized bed). Illustrative and non-limiting shapes and forms include powder, round or spherical (e.g., a sphere), ellipsoidal, pellet, bead, cylinder, granule (e.g., regular and/or irregular), trilobe, quadrilobe, ring, wagon wheel, monolith, and the like, as well as any combination thereof. Accordingly, various methods can be utilized to prepare the supported chromium precursor, the solid support, the supported chromium catalyst, and the reduced chromium catalyst particles, including, for example, extrusion, spray drying, pelletizing, marumerizing, spherodizing, agglomeration, oil drop, and the like, as well as combinations thereof.

In some aspects, the supported chromium precursor, the solid support, the supported chromium catalyst, and the reduced chromium catalyst have a relatively small particle size, in which representative ranges for the average (d50) particle size of the supported chromium catalyst and the reduced chromium catalyst can include from about 10 to about 500 microns, from about 25 to about 250 microns, from about 20 to about 100 microns, from about 40 to about 160 microns, or from about 40 to about 120 microns.

In other aspects, the supported chromium precursor, the solid support, the supported chromium catalyst, and the reduced chromium catalyst can be in the form of pellets or beads—and the like—having an average size ranging from about 1/16 inch to about 1/2 inch, or from about 1/8 inch to about 1/4 inch. As noted above, the size of the catalyst particles can be varied to suit the particular process for converting the hydrocarbon reactant into the alcohol compound and/or carbonyl compound.

Supported catalysts also are encompassed herein. In one aspect, a first supported catalyst can comprise a solid support and a chromate compound in an amount from about 0.1 to about 25 wt. % of chromium, based on the weight of the catalyst. Illustrative and non-limiting examples of suitable chromate compounds include potassium chromate, sodium chromate, ammonium chromate, potassium dichromate, sodium dichromate, ammonium dichromate, and the like, as well as any combination thereof. In another aspect, a second supported catalyst can comprise a solid support, from about 0.1 to about 25 wt. % of chromium, and from about 0.1 to about 25 wt. % of an alkali metal, based on the weight of the catalyst, wherein at least one bonding site on the chromium has a ligand characterized by the following formula: —O-Hydrocarbon group (for example, an alkoxy group can be bonded to the chromium). Typically, the molar ratio of the hydrocarbon group to chromium in the second supported catalyst can be from about 0.25:1 to about 2:1, from about 0.5:1 to about 2:1, from about 0.5:1 to about 1.5:1, from about 0.75:1 to about 1.75:1, or from about 0.75:1 to about 1.25:1. Additionally or alternatively, the second supported catalyst can comprise chromium having an average valence of less than or equal to about 5.25 in one aspect, less than or equal to about 5 in another aspect, less than or equal to about 4.75 in another aspect, less than or equal to about 4.5 in another aspect, less than or equal to about 4.25 in yet another aspect, or less than or equal to about 4 in still another aspect. These first and second supported catalysts also can have any of the features provided below and in any combination.

The solid support for the first and second supported catalysts can comprise any solid support disclosed herein, such as a solid oxide (e.g., silica, silica-titania, or silica-coated alumina), a chemically-treated solid oxide (e.g., sulfated alumina or fluorided silica-coated alumina), a zeolite, a clay, an activated carbon, or any combination thereof. In a particular aspect, the solid support can comprise a silica-coated alumina, which can have any weight ratio of alumina to silica disclosed herein, including from 1:20 to about 20:1, from about 1:5 to about 5:1, from about 3:1 to about 1:3, from about 1:1 to about 3:1, from about 1:1 to about 2:1, from about 1.2:1 to about 1.8:1, and the like.

The amount of chromium in the first and second supported catalysts is not particularly limited, but often ranges from about 0.1 to about 25 wt. %. Therefore, suitable ranges include from about 0.25 to about 15 wt. %, from about 0.5 to about 5 wt. %, from about 2 to about 20 wt. %, or from about 3 to about 15 wt. % of chromium, based on the weight of the respective supported catalyst. Likewise, the amount of alkali metal is not particularly limited, but the first and second supported catalysts typically contain (based on the weight of the respective catalyst) from about 0.1 to about 25 wt. % alkali metal; alternatively, from about 0.25 to about 15 wt. % alkali metal; alternatively, from about 0.5 to about 5 wt. % alkali metal; alternatively, from about 2 to about 20 wt. % alkali metal; or alternatively, from about 3 to about 15 wt. % alkali metal.

Examples 1-67

The invention is further illustrated by the following examples, which are not to be construed in any way as imposing limitations to the scope of this invention. Various other aspects, modifications, and equivalents thereof, which after reading the description herein, can suggest themselves to one of ordinary skill in the art without departing from the spirit of the present invention or the scope of the appended claims.

Catalyst A was a Cr/silica catalyst containing 1 wt. % Cr, with a BET surface area of 500 m$^2$/g, a pore volume of 1.6 mL/g, and an average particle size of 100 μm. Prior to use, the catalyst was calcined in air at 650° C. for 3 hr to form the chromium (VI)/silica catalyst containing 0.97 wt. % hexavalent Cr.

Catalyst B was a Cr/silica-titania catalyst containing 1 wt. % Cr and 4.2 wt. % TiO$_2$, with a BET surface area of 500 m$^2$/g, a pore volume of 2.5 mL/g, and an average particle size of 130 μm. Prior to use, the catalyst was calcined in air at 850-870° C. for 3 hr to form the chromium (VI)/silica-titania catalyst containing 0.95 wt. % hexavalent Cr.

Catalyst C was a Cr/silica containing 10 wt. % Cr, the silica having a BET surface area of 500 m$^2$/g, a pore volume of 1.6 mL/g, and an average particle size of 100 μm. Prior to use, the catalyst was calcined in air at 400° C. for 3 hr to form the chromium (VI)/silica catalyst containing 5 wt. % hexavalent Cr.

Catalyst D was a Cr/silica-titania containing 0.8 wt. % Cr and 7.5 wt. % TiO$_2$, with a BET surface area of 550 m$^2$/g, a pore volume of 2.5 mL/g, and an average particle size of 130 μm. Prior to use, the catalyst was calcined in air at 850° C. for 3 hr to form the chromium (VI)/silica-titania catalyst containing 0.8 wt. % hexavalent Cr.

Catalyst E was a Cr/silica containing 0.28 wt. % Cr, with a BET surface area of 500 m$^2$/g, a pore volume of 1.6 mL/g, and an average particle size of 100 μm. Prior to use, the catalyst was calcined in air at 750° C. for 3 hr to form the chromium (VI)/silica catalyst containing 0.28 wt. % hexavalent Cr.

Catalyst F was a Cr/silica containing 5 wt. % Cr, with a BET surface area of 500 m$^2$/g, a pore volume of 1.6 mL/g, and an average particle size of 100 μm. Prior to use, the catalyst was calcined in air at 500° C. for 3 hr to form the chromium (VI)/silica catalyst containing 4 wt. % hexavalent Cr.

Catalysts G1-G2 were prepared by dissolving CrO$_3$ in water, then impregnating the resulting solution onto an alumina (boehmite) with a BET surface area of 300 m$^2$/g and a pore volume of 1.3 mL/g to equal 5 wt. % Cr. After drying and prior to use, the catalysts were calcined in air at 500° C. (G1) or 600° C. (G2) for 3 hr to form the chromium (VI)/alumina catalysts containing 4.5 wt. % hexavalent Cr.

Catalysts H1-H2 were prepared by dissolving CrO$_3$ in water, then impregnating the resulting solution onto a silica-coated alumina (40 wt. % silica, BET surface area of 450 m$^2$/g, pore volume of 1.4 mL/g, average particle size of 25 μm) to equal 5 wt. % Cr. After drying and prior to use, the catalysts were calcined in air at 500° C. (H1) or 600° C. (H2) for 3 hr to form the chromium (VI)/silica-coated alumina catalysts.

Catalyst J was prepared by dissolving K$_2$Cr$_2$O$_7$ in water, then impregnating the resulting solution onto a silica (BET surface area of 500 m$^2$/g, pore volume of 1.6 mL/g, average particle size of 100 μm) to equal 5 wt. % Cr. After drying and prior to use, the catalyst was calcined in air at 500° C. for 3 hr to form the chromium (VI)/silica catalyst containing 5 wt. % hexavalent Cr.

Catalyst K was prepared by dissolving K$_2$Cr$_2$O$_7$ in water, then impregnating the resulting solution onto a silica (BET surface area of 500 m$^2$/g, pore volume of 1.6 mL/g, average particle size of 100 μm) to equal 10 wt. % Cr. After removing excess water, the catalyst was heat treated in air at 100° C. for 3 hr to form the chromium (VI)/silica catalyst containing 10 wt. % hexavalent Cr.

Catalyst L was prepared by dissolving K$_2$Cr$_2$O$_7$ in water, then impregnating the resulting solution onto a silica (BET surface area of 500 m$^2$/g, pore volume of 1.6 mL/g, average particle size of 100 μm) to equal 10 wt. % Cr. After removing excess water, the catalyst was heat treated in air at 200° C. for 3 hr to form the chromium (VI)/silica catalyst containing 10 wt. % hexavalent Cr.

BET surface areas can be determined using the BET nitrogen adsorption method of Brunauer et al., *J. Am. Chem. Soc.,* 60, 309 (1938) as described in ASTM D1993-91. Total pore volumes can be determined in accordance with Halsey, G. D., *J. Chem. Phys.* (1948), 16, pp. 931. The d50 particle size, or median or average particle size, refers to the particle size for which 50% of the sample by volume has a smaller size and 50% of the sample has a larger size, and can be determined using laser diffraction in accordance with ISO 13320.

Table I summarizes the reactions of Examples 1-67, in which the supported chromium catalyst was first charged to an air-tight glass container at 25° C. (or a different temperature if specified), followed by the addition of the hydrocarbon reactant. The glass container was then exposed to a light source as noted in Table I. For all examples where the glass container was exposed to light, the container was slowly rotated at 5-10 rpm to turn over the catalyst particles in the bottle to ensure even exposure of the mixture of the supported chromium catalyst and the hydrocarbon reactant to each other and to the light. Samples exposed to sunlight were taken outside and placed in direct sunlight. For examples where the glass container was exposed to artificial light, the sample was placed in a box containing a fluorescent light or a LED light, where three 15 watt bulbs were placed in a plane about 3 inches apart and about 2 inches from the bottle. Reduction of the supported chromium catalysts was monitored by the presence of a color change. Each supported chromium catalyst comprising chromium in the hexavalent oxidation state had an orange color which darkened significantly upon exposing the supported chromium catalyst to light in the presence of the hydrocarbon reactant, and usually assuming a green or blue color, indicating reduction of the supported chromium catalyst starting material, and formation of the reduced chromium catalyst.

After the desired exposure time, the reduced chromium catalyst was mixed with a hydrolysis agent to cleave the hydrocarbon-containing ligand from the reduced chromium catalyst. The mixture was stirred for several minutes. The hydrolysis agent used was generally selected so as to not interfere with analysis of the reaction product (e.g., methanol was not used as the hydrolysis agent when the reaction product after hydrolysis could contain methanol, etc.).

Table I summarizes the results of Examples 1-67, and lists the specific supported chromium catalyst and amount, the hydrocarbon reactant and amount, the light treatment and resulting color, the hydrolysis agent and amount, the acid/Cr (molar), alcohol/Cr (molar), the GC-MS/Cr (molar), the total/Cr (molar), and an analysis of the reaction product (oxygenated products) after hydrolysis. The reaction product analysis includes only oxygen-containing products that were derivable from the reductant/reactant and does not include, for example, materials resulting from the hydrolysis agent or its by-products, or oligomers resulting from polymerization. For the oxygenated reaction products, area % from the analytical procedures listed below is roughly equivalent to mol %, thus the results in Table I are shown in mol %.

Carboxylic acid products (and acid/Cr ratios on a molar basis) were determined by first neutralizing the product acids with a solution of sodium hydroxide to put them into the ionic form. Then, a small amount of the sample was injected through an ion column designed to separate anions from weak organic acids through an ion chromatography process. A Dionex IC-3000 instrument with an ICE-AS1 column and guard was used. The test was specifically sensitive to linear carboxylic acids from $C_1$ to $C_6$, glutarate and glycolate ions. Results were reported in micrograms of carboxylate per mL of solution, which was then converted to moles.

Lower alcohol products (and alcohol/Cr on a molar basis) were determined using a GC-MS procedure, with an Agilent 6890 gas chromatograph having a flame-ionizing detector (FID). It used a Restek Stapilwax column (P/N 10658) designed and gated specifically to separate and detect light alcohols. The procedure was gated for acetone, methanol, ethanol, isopropanol, n-propanol, isobutanol, n-butanol, t-butanol, 2-butanol, 2-butoxyethanol, acetonitrile and tetrahydrofuran.

Additional reaction products (and GC-MS/Cr on a molar basis) were determined using another GC-MS procedure, as follows. Gas chromatography was performed using an Agilent 7890B GC equipped with both flame ionizing and mass spectral analysis. An all-purpose capillary column (Agilent J&W VF-5 ms, 30 m×0.25 mm×0.25 μm) was used with variable temperature. Approximate 0.5 μL sample aliquots were injected into a GC port held at 250° C. using a split ratio of 10:1. The carrier gas was ultra-high purity helium and was electronically controlled throughout the run to a constant flow rate of 1.2 mL/min. Initial column temperature was held at 50° C. for 5 min, ramped at 20° C./min to 250° C., and then held at 250° C. for 19 min. Spectral assignment was made via mass correlation using an Agilent 5977B mass spectrometer connected to the GC unit using electron ionization at 70 eV. The nominal mass range scanned was 14-400 m/z using a scan time of 0.5 sec. Nominal detector voltage used was 1200 V. For calibration purposes both the FID and MS detectors were sometimes used in sequence on the same or reference samples.

Due to the wide range of oxygenated products produced herein, one or all of these three procedures were used to characterize the reaction product after hydrolysis. In some cases, the same compound was detected by more than one technique, and this was subtracted out of the total/Cr (on a molar basis) to prevent double counting of the same compound by more than one analytical technique. For the most part, however, there was very little overlap between the three analytical procedures.

Referring now to the data in Table I, Examples 1-10 demonstrate the unexpected conversion of methane into methanol at ambient temperature using a variety of supported chromium catalysts, irradiation treatments, and hydrolysis agents. Note that Examples 1-4 used only one analytical technique and showed a product stream that was 100% methanol, whereas Examples 6-10 used all three analytical techniques and resulted in product streams containing 66-97 mol % methanol, the balance being formic acid.

Similar successful results were found for the conversion of ethane into ethanol, isobutane into t-butanol/i-butanol, n-pentane into 2-pentanol/1-pentanol, cyclopentane into cyclopentanol, n-hexane into various hexanols, cyclohexane into cyclohexanol, and toluene into benzaldehyde/benzyl alcohol. When the hydrocarbon reactant was i-pentane, the oxygenated reaction product contained a variety of alcohol and carbonyl products, whereas when the reactant was dichloromethane, no conversion to an alcohol or carbonyl was noted. While the focus of these examples was not to maximize chromium conversion (or yield to any particular alcohol or carbonyl compound), the total/Cr molar value in Table I illustrates that significant chromium conversion and alcohol/carbonyl yield can be achieved, depending of course on the reductant, the catalyst (and chromium loading), and the irradiation conditions, among other factors.

When the reactant was an olefin, it was found that the GC-MS analytical technique was necessary to identify diol products, thus examples in which this technique was not used may give an incomplete representation of the oxygenated product mix. Generally, examples that utilized ethylene as the reductant formed a reaction product (even when used at −78° C. to prevent polymerization) after hydrolysis that included ethanediol and methanol, ethanol, formic acid, and/or acetic acid. The lower reaction temperatures seemed to favor selectivity to the diol. Examples that utilized 1-pentene as the reductant formed a reaction product (even with no light irradiation, see Example 44) after hydrolysis that included a pentanediol (e.g., 1,2-pentanediol) and various acids and other alcohols. Examples that utilized 1-hexene or 2-hexene as the reductant formed a reaction product (even with no light irradiation, see Example 55) after hydrolysis that included a hexanediol (e.g., 1,2-hexanediol and/or 3,4-hexanediol) and various acids and other alcohols. Table I demonstrates that these olefins are very reactive and, therefore, the reaction product typically contained a mixture of mono-alcohols, diols, aldehydes, ketones, and/or carboxylic acids.

Of particular interest, and unexpectedly, the chromate catalysts (Catalysts J-L) very effectively converted hydrocarbons into alcohols and/or carbonyls, despite low heat treatment temperatures (100-500° C.). Also, catalysts with high loadings of 5-10 wt. % chromium, such as Catalysts C and F-L, often had relatively low "total/Cr" molar yields, but when multiplied by a factor of 5-10 to compare to a 1 wt. % chromium catalyst, these high chromium catalysts produced an exceptional amount of alcohol and/or carbonyl products.

TABLE 1

Summary of Examples 1-67 (products in mol %)

| Example | 1 | | 2 | | 3 | | 4 | |
|---|---|---|---|---|---|---|---|---|
| Catalyst | A | | B | | A | | B | |
| Weight (g) | 2.7 | | 2.0 | | 1.8 | | 2.0 | |
| Reductant | Methane | | Methane | | Methane | | Methane | |
| Amount | 10 psig | | 10 psig | | 10 psig | | 10 psig | |
| Light | 4 hr Sun | | 4 hr Sun | | 6 hr Sun | | 6 hr Sun | |
| Color | Green | | Green | | Green | | Green | |
| Hydrolysis | $H_2O$/Ether | | $H_2O$/Ether | | $H_2O$ | | $H_2O$ | |
| Amount (mL) | 20 | | 20 | | 20 | | 20 | |
| Acid/Cr | 0 | | | | 0 | | 0 | |
| Alcohol/Cr | 1.013 | | 0.272 | | 0.261 | | 0.173 | |
| GC-MS/Cr | | | | | | | | |
| Total/Cr | 1.013 | | 0.272 | | 0.261 | | 0.173 | |
| Oxygenated Products | methanol | 100% | methanol | 100% | methanol | 100% | methanol | 100% |

| Example | 5 | | 6 | | 7 | | 8 | |
|---|---|---|---|---|---|---|---|---|
| Catalyst | D | | E | | J | | F | |
| Weight (g) | 2.1 | | 2.8 | | 2.2 | | 2.1 | |
| Reductant | Methane | | Methane | | Methane | | Methane | |
| Amount | 15 psig | | 15 psig | | 15 psig | | 15 psig | |
| Light | 44 hr Blue | | 67 hr Blue | | 67 hr Blue | | 67 hr Blue | |
| Color | Olive green | | Olive green | | Red-brown | | Dark brown-black | |
| Hydrolysis | $H_2O$ + $CH_3CN$ | | $H_2O$ + $CH_3CN$ | | $H_2O$ + $CH_3CN$ | | $H_2O$ + $CH_3CN$ | |
| Amount (mL) | 15 | | 15 | | 15 | | 15 | |
| Acid/Cr | 0.009 | | 0.010 | | 0.007 | | 0.008 | |
| Alcohol/Cr | 0.284 | | 0.320 | | 0.030 | | 0.073 | |
| GC-MS/Cr | 0.007 | | 0.000 | | 0 | | 0.025 | |
| Total/Cr | 0.300 | | 0.330 | | 0.037 | | 0.081 | |
| Oxygenated Products | methanol<br>formic acid | 96%<br>4% | methanol<br>formic acid | 97%<br>3% | methanol<br>formic acid | 80%<br>20% | methanol<br>formic acid | 90%<br>10% |

| Example | 9 | 10 | 11 | 12 |
|---|---|---|---|---|
| Catalyst | H2 | G2 | D | B |
| Weight (g) | 2.2 | 2.0 | 2.0 | 2.1 |
| Reductant | Methane | Methane | Dichloromethane | Ethane |
| Amount | 15 psig | 15 psig | 0.5 mL | 15 psig |
| Light | 67 hr Blue | 67 hr Blue | 7 hr Blue | 72 hr Blue |
| Color | Dark brown | Dark brown | Olive Green | Blue-gray |
| Hydrolysis | $H_2O$ + $CH_3CN$ | $H_2O$ + $CH_3CN$ | 10% $H_2O$/MeOH | $H_2O$ |
| Amount (mL) | 15 | 15 | 40 | 20 |

TABLE 1-continued

Summary of Examples 1-67 (products in mol %)

| | | | | | | | | |
|---|---|---|---|---|---|---|---|---|
| Acid/Cr | 0.003 | | 0.002 | | | | 0.042 | |
| Alcohol/Cr | 0.025 | | 0.004 | | | | 0.366 | |
| GC-MS/Cr | 0.000 | | 0.000 | | 0.000 | | 0.000 | |
| Total/Cr | 0.028 | | 0.006 | | 0.000 | | 0.408 | |
| Oxygenated | methanol | 91% | methanol | 66% | No Products | | ethanol | 72% |
| Products | formic acid | 9% | formic acid | 34% | Detected | | methanol | 16% |
| | | | | | | | formic acid | 6% |
| | | | | | | | hexanoic acid | 3% |
| | | | | | | | acetic acid | 1% |
| | | | | | | | pentanoic acid | 1% |

| Example | 13 | | 14 | | 15 | | 16 | |
|---|---|---|---|---|---|---|---|---|
| Catalyst | D | | D | | B | | B | |
| Weight (g) | 1.9 | | 2.5 | | 2.6 | | 1.9 | |
| Reductant | Ethane | | i-Butane | | n-Pentane | | n-Pentane | |
| Amount | 15 psig | | 10 psig | | 0.75 mL | | 0.75 mL | |
| Light | 30 hr Blue | | 6 hr UV | | 1 hr UV | | 3.3 hr UV | |
| Color | Blue-gray | | Green | | Blue-gray | | Blue-gray | |
| Hydrolysis | $H_2O + CH_3CN$ | | 4% $H_2O$/MeOH | | 10% $H_2O$/MeOH | | 10% $H_2O$/MeOH | |
| Amount (mL) | 15 | | 15 | | 12 | | 12 | |
| Acid/Cr | 0.013 | | 0.000 | | | | | |
| Alcohol/Cr | 0.374 | | 0.258 | | | | | |
| GC-MS/Cr | 0.009 | | 0.465 | | 0.270 | | 0.500 | |
| Total/Cr | 0.383 | | 0.723 | | 0.270 | | 0.500 | |
| Oxygenated | ethanol | 90% | t-butanol | 40% | 2-pentanol | 49% | 2-pentanol | 47% |
| Products | methanol | 6% | i-butanol | 28% | 2-pentanone | 33% | 2-pentanone | 36% |
| | acetic acid | 3% | acetone | 10% | 1-pentanol | 18% | 1-pentanol | 17% |
| | isopropanol | 1% | isopropanol | 5% | | | | |
| | n-propanol | 1% | isobutanal | 5% | | | | |

| Example | 17 | | 18 | | 19 | | 20 | |
|---|---|---|---|---|---|---|---|---|
| Catalyst | C | | D | | E | | D | |
| Weight (g) | 1.9 | | 2.0 | | 2.6 | | 2.0 | |
| Reductant | n-Pentane | | n-Pentane | | n-Pentane | | n-Pentane | |
| Amount | 0.5 mL | | 0.5 mL | | 2 mL | | 2 mL | |
| Light | 3 hr Blue | | 7 hr Blue | | 26 hr UV | | 26 hr UV | |
| Color | Black | | Blue-gray | | Blue-gray | | Blue-gray | |
| Hydrolysis | 10% $H_2O$/MeOH | | Vitamin C | | 5% $H_2O$/MeOH | | 5% $H_2O$/MeOH | |
| Amount (mL) | 11 | | 30 | | 10 | | 10 | |
| Acid/Cr | 0.000 | | 0.000 | | 0.000 | | 0.042 | |
| Alcohol/Cr | | | | | 0.000 | | 0.000 | |
| GC-MS/Cr | 0.207 | | 1.140 | | 0.143 | | 0.499 | |
| Total/Cr | 0.207 | | 1.140 | | 0.143 | | 0.541 | |
| Oxygenated | 2-pentanone | 62% | 2-pentanol | 63% | 2-pentanol | 41% | 2-pentanol | 39% |
| Products | 2-pentanol | 14% | 1-pentanol | 19% | 1-pentanol | 23% | 1-pentanol | 21% |
| | 3-pentanone | 10% | pentanal | 18% | 2-pentanone | 21% | 2-pentanone | 15% |
| | 3-penten-2-one | 3% | | | 3-pentanone | 11% | 3-pentanone | 10% |
| | 1-pentanol | 2% | | | C10H18O | 4% | formic acid | 8% |
| | | | | | | | 3-penten-2-one | 2% |
| | | | | | | | 2-pentenal | 2% |

| Example | 21 | | 22 | | 23 | | 24 | |
|---|---|---|---|---|---|---|---|---|
| Catalyst | L | | D | | E | | D | |
| Weight (g) | 3.0 | | 1.9 | | 2.3 | | 1.1 | |
| Reductant | n-Pentane | | i-Pentane | | i-Pentane | | i-Pentane | |
| Amount | 2 mL | | 0.5 mL | | 0.5 mL | | 2 mL | |
| Light | UV 24 h | | 7 hr Blue | | 31 hr Blue | | 4.5 hr UV | |
| Color | Brown | | Blue-gray | | Blue-gray | | Gray-blue | |
| Hydrolysis | 4% $H_2O$/MeOH | | 10% $H_2O$/MeOH | | $H_2O + CH_3CN$ | | 5% $H_2O$/MeOH | |
| Amount (mL) | 15 | | 40 | | 15 | | 15 | |
| Acid/Cr | 0.002 | | 0.000 | | 0.000 | | 0.006 | |
| Alcohol/Cr | 0.005 | | | | | | 0.347 | |
| GC-MS/Cr | 0.077 | | 0.850 | | 0.929 | | 0.600 | |
| Total/Cr | 0.083 | | 0.850 | | 0.929 | | 0.953 | |
| Oxygenated | 2-pentanol | 40% | t-pentanol | 24% | 2-pentanol | 31% | ethanol | 27% |
| Products | 2-pentanone | 21% | 3-Me-2-butanol | 23% | acetic acid | 23% | 2-Me-1-butanol | 18% |
| | 1-pentanol | 15% | Me-butanol | 22% | 2-pentanol | 22% | t-pentanol | 17% |
| | 3-pentanone | 9% | isoamyl alcohol | 13% | 3-pentanol | 11% | 3-Me-2-butanol | 10% |

TABLE 1-continued

Summary of Examples 1-67 (products in mol %)

| | isopropanol | 4% | 2-Me-butanal | 11% | C5H4O3 | 7% | isoamyl alcohol | 9% |
|---|---|---|---|---|---|---|---|---|
| | C10H18O | 2% | 3-Me-2-butanone | 7% | | | isobutanol | 8% |
| | C7H14O | 2% | | | | | 3-Me-2-butanone | 6% |
| | formic acid | 2% | | | | | C6H12O3 | 3% |

| Example | 25 | 26 | 27 | 28 |
|---|---|---|---|---|
| Catalyst | J | F | H1 | G1 |
| Weight (g) | 2.2 | 2.4 | 1.9 | 1.9 |
| Reductant | i-Pentane | i-Pentane | i-Pentane | i-Pentane |
| Amount | 0.5 mL | 0.5 mL | 0.5 mL | 0.5 mL |
| Light | 31 hr Blue | 31 hr Blue | 40 hr Blue | 40 hr Blue |
| Color | Dark red | Blue-gray-black | Green-brown | Green-brown |
| Hydrolysis | $H_2O + CH_3CN$ | $H_2O + CH_3CN$ | $H_2O + CH_3CN$ | $H_2O + CH_3CN$ |
| Amount (mL) | 15 | 15 | 15 | 15 |
| Acid/Cr | 0.004 | 0.004 | 0.004 | 0.016 |
| Alcohol/Cr | | | | |
| GC-MS/Cr | 0.744 | 0.042 | 0.061 | 0.052 |
| Total/Cr | 0.747 | 0.046 | 0.064 | 0.068 |
| Oxygenated Products | 2-Me-2-butanol 41% | 3-Me-1-butanol 26% | C5H12O alcohol 25% | C5H12O alcohol 23% |
| | 3-Me-2-butanol 21% | 2-Me-1-butanol 24% | C5H8O aldehyde 22% | 2-Me-2-butenal 23% |
| | 2-Me-1-butanol 15% | 2-Me-2-butenal 24% | C5H12O 17% | C5H12O2 13% |
| | 3-Me-2-butanone 9% | 3-Me-2-butenal 5% | 3-Me-2-pentanone 5% | formic acid 12% |
| | 3-Me-1-butanol 9% | acetic acid 4% | C5H12O2 5% | C5H12O 12% |
| | C10/C11 dioxygenate 2% | C5H10O 24% | C6H10O 4% | acetic acid 11% |
| | | formic acid | 4-OH-3-Me-2-butanone 4% | 2-pentenal 2% |
| | | | formic acid 3% | |
| | | | C5H10O 3% | |
| | | | 3-Me-2 butenal 2% | |
| | | | acetic acid 2% | |

| Example | 29 | 30 | 31 | 32 |
|---|---|---|---|---|
| Catalyst | D | B | B | B |
| Weight (g) | 2.1 | 2.1 | 1.2 | 1.5 |
| Reductant | Cyclopentane | n-Hexane | Cyclohexane | Decalin |
| Amount | 0.5 mL | 0.5 mL | | 0.5 g |
| Light | 7 hr Blue | 3.3 hr UV | 2 hr Blue LED | 2 hr Blue LED |
| Color | Blue-gray | Blue-gray | Deep blue | Light blue |
| Hydrolysis | 10% $H_2O$/MeOH | 10% $H_2O$/MeOH | 10% $H_2O$/MeOH | 10% $H_2O$/MeOH |
| Amount (mL) | 40 | 12 | 12 | 12 |
| Acid/Cr | 0.000 | | No data | No data |
| Alcohol/Cr | | | No data | No data |
| GC-MS/Cr | 0.606 | 0.573 | No data | No data |
| Total/Cr | 0.606 | 0.573 | | |
| Oxygenated Products | cyclopentanol 85% | 2-hexanol 25% | cyclohexanol 49% | decalols, C10H18O 77% |
| | cyclopentanone 15% | 2-hexanone 23% | cyclohexanone 40% | decalones, C10H18O 17% |
| | | 3-hexanol 20% | 2-cyclohexen-1-one 7% | C10H14O 2% |
| | | 3-hexanone 17% | cyclohexanediol 2% | C10H14O2 1% |
| | | 1-hexanol 15% | C14H22O 1% | naphthalenone 1% |
| | | | C6H10O2 1% | |

| Example | 33 | 34 | 35 | 36 |
|---|---|---|---|---|
| Catalyst | B | B | K | A |
| Weight (g) | 1.1 | 1.6 | 3.3 | 2.0 |
| Reductant | Adamantane | Toluene | Toluene | Ethylene |
| Amount | 0.5 g | 0.5 mL | 2 mL | 10 psig |
| Light | 2 hr Blue LED | 1.5 hr Blue | UV 24 h | 9 hr Sun |
| Color | Blue | Blue-black | Brown | Blue-gray |
| Hydrolysis | 10% $H_2O$/MeOH | 10% $H_2O$/MeOH | 4% $H_2O$/MeOH | $H_2O$ |
| Amount (mL) | 12 | 6 | 15 | 20 |
| Acid/Cr | No data | | 0.001 | 0.096 |
| Alcohol/Cr | No data | | 0.003 | 0.108 |
| GC-MS/Cr | No data | 0.567 | 0.129 | |
| Total/Cr | | 0.567 | 0.133 | 0.204 |

TABLE 1-continued

Summary of Examples 1-67 (products in mol %)

| Oxygenated Products | adamantanone | 32% | benzaldehyde | 41% | benzaldehyde | 77% | methanol | 51% |
|---|---|---|---|---|---|---|---|---|
| | adamantanol | 25% | benzyl alcohol | 17% | benzyl alcohol | 20% | formic acid | 46% |
| | adamantan-2-ol | 20% | C14H12O | 9% | isopropanol | 2% | n-propanol | 2% |
| | C10H14O | 16% | benzophenone | 8% | formic acid | 1% | acetic acid | 1% |
| | adamantanediol | 2% | C14H12O | 6% | | | | |
| | C11H20O | 1% | C14H12O | 6% | | | | |
| | | | 4-Me phenol | 5% | | | | |
| | | | 2-Me phenol | 5% | | | | |

| Example | 37 | 38 | 39 | 40 |
|---|---|---|---|---|
| Catalyst | B | D | D | D |
| Weight (g) | 2.1 | 2.4 | 2.1 | 2.1 |
| Reductant | Ethylene | Ethylene | Ethylene | Ethylene |
| Amount | 10 psig | 15 psig (−78 C.) | 15 psig (−78 C.) | 15 psig (−78 C.) |
| Light | 9 hr Sun | 60 hr Blue | 24 hr Blue | 24 hr Blue |
| Color | Blue-gray | Blue-green | Blue-green | Blue-green |
| Hydrolysis | 0.1N NaOH | 0.1N NaOH | 0.1N NaOH | 0.1N NaOH |
| Amount (mL) | 20 | 15 | 15 | 15 |
| Acid/Cr | 0.233 | 0.110 | 0.136 | 0.144 |
| Alcohol/Cr | 0.101 | 0.162 | 0.111 | 0.401 |
| GC-MS/Cr | | 0.035 | 0.071 | 0.162 |
| Total/Cr | 0.335 | 0.272 | 0.318 | 0.675 |

| Oxygenated Products | formic acid | | formic acid | 68% | formic acid | 39% | ethanediol | 48% | ethanediol | 72% |
|---|---|---|---|---|---|---|---|---|---|---|
| | methanol | | methanol | 28% | ethanediol | 29% | formic acid | 25% | formic acid | 20% |
| | acetic acid | | ethanediol | 1% | methanol | 27% | diethylene glycol | 24% | diethylene glycol | 4% |
| | ethanol | | ethanol | 1% | ethanol | 2% | methanol | 2% | methanol | 2% |
| | | | acetic acid | | n-propanol | 1% | acetic acid | 1% | acetic acid | 1% |
| | | | n-propanol | | propionic acid | 1% | ethanol | 1% | ethanol | 1% |
| | | | | | acetic acid | 1% | | | | |

| Example | 41 | 42 | 43 | 44 |
|---|---|---|---|---|
| Catalyst | E | D | D | D |
| Weight (g) | 2.3 | 2.0 | 1.5 | 2.1 |
| Reductant | Ethylene | Ethylene | 1-Pentene | 1-Pentene |
| Amount | 15 psig | 15 psig | 0.5 mL | 0.5 mL |
| Light | 24 hr UV | 24 hr UV | 14 hr Blue | Dark—24 hr |
| Color | | | Blue-gray | |
| Hydrolysis | H2O + CH3CN | H2O + CH3CN | H2O | H2O |
| Amount (mL) | 15 | 15 | 20 | 15 |
| Acid/Cr | 0.461 | 0.181 | 0.245 | 0.012 |
| Alcohol/Cr | 0.136 | 0.069 | | 0.044 |
| GC-MS/Cr | 0.017 | 0.190 | 1.047 | 0.016 |
| Total/Cr | 0.614 | 0.436 | 1.193 | 0.072 |

| Oxygenated Products | | | | | | | | | | |
|---|---|---|---|---|---|---|---|---|---|---|
| | acetic acid | | formic acid | 38% | C8H18O | 35% | 1-butanol | 17% | 1-butanol | 29% |
| | formic acid | | ethanediol | 36% | formic acid | 32% | formic acid | 13% | formic acid | 14% |
| | methanol | | methanol | 19% | C10 or C11 alcohol | 12% | n-propanol | 12% | n-propanol | 9% |
| | ethanediol | | diethylene glycol | 2% | 1,2-pentanediol | 11% | ethanediol | 7% | ethanediol | 8% |
| | ethanol | | acetic acid | 2% | C9H20O | 6% | 1,2-pentanediol | 7% | 1,2-pentanediol | 8% |
| | n-propanol | | ethanol | 1% | C8-C10 alcohol | 3% | methanol | 6% | methanol | 8% |
| | | | | | 2-heptanone | | 2-pentenal | 5% | 2-pentenal | 7% |
| | | | | | C7H14O3 | | acetone | 4% | acetone | 5% |
| | | | | | C10H22O | | 2-penten-1-ol | 4% | 2-penten-1-ol | 3% |
| | | | | | isoamyl alcohol | | ethanol | 3% | ethanol | 2% |
| | | | | | acetic acid | 3% | | | | |
| | | | | | 3-pentanol | 2% | | | | |

| Example | 45 | 46 | 47 | 48 |
|---|---|---|---|---|
| Catalyst | D | D | D | D |
| Weight (g) | 2.0 | 1.9 | 1.7 | 1.5 |
| Reductant | 1-Pentene | 1-Pentene | 1-Hexene | 1-Hexene |
| Amount | 0.5 mL | 0.5 mL | 0.5 mL | 0.5 mL |
| Light | 24 hr UV | 2 hr UV | 7 hr Blue | 14 hr Blue |
| Color | Magenta | Sky blue | Blue-gray | Blue-gray |
| Hydrolysis | H2O | H2O | 10% H2O/MeOH | H2O |
| Amount (mL) | 15 | 15 | 40 | 20 |
| Acid/Cr | 0.015 | 0.018 | 0.036 | 0.248 |
| Alcohol/Cr | 0.000 | 0.091 | | |
| GC-MS/Cr | 0.087 | 0.124 | | 1.315 |
| Total/Cr | 0.102 | 0.233 | 0.036 | 1.548 |

| Oxygenated Products | 1,2-pentanediol | | 1-butanol | 31% | formic acid | 20% | hexanoic acid | 41% |
|---|---|---|---|---|---|---|---|---|
| | 2-pentenal | | 1,2-pentanediol | 13% | | 17% | formic acid | 10% |
| | formic acid | | 2-pentenal | 11% | | 11% | 2-hexanone | 8% |

TABLE 1-continued

Summary of Examples 1-67 (products in mol %)

| | | | | | | | |
|---|---|---|---|---|---|---|---|
| C10H22O | 10% | n-propanol | 7% | | | 2-octanone | 3% |
| C5H10O2 | 5% | ethanediol | 7% | | | 1,2-hexanediol | 3% |
| 2-heptanone | 5% | formic acid | 6% | | | 1-hexen-3-ol | 3% |
| C8-11 oxygenate | 3% | ethyl ether propanoic | 5% | | | 3-penten-2-ol | 3% |
| C8-10 oxygenate | 3% | acid | | | | Me-nonanol | 2% |
| C9-11 oxygenate | 3% | 2-penten-1-ol | 5% | | | Me-heptanol | 2% |
| C5 di-oxygenate | 2% | ethanol | 3% | | | butyric acid | 2% |
| C10H20O | 2% | 2-heptanone | 2% | | | 2-hexanol | 2% |
| | | methanol | 2% | | | 2-hexenal | 2% |
| | | 2-Me-2-pentenal | 2% | | | | |

| Example | 49 | 50 | 51 | 52 |
|---|---|---|---|---|
| Catalyst | D | D | D | D |
| Weight (g) | 2.1 | 2.1 | 2.0 | 1.2 |
| Reductant | 1-Hexene | 1-Hexene | 1-Hexene | 1-Hexene |
| Amount | 0.5 mL | 0.5 mL | 0.5 mL | 2 mL |
| Light | 14 hr Blue | 31 hr Blue | 31 hr Blue | 4.5 hr UV |
| Color | Blue-gray | Blue-gray | Blue-gray | Blue-green |
| Hydrolysis | Vitamin C | $H_2O + CH_3CN$ | 0.1N HCl + $Fe^{+2}$ | 5% $H_2O$/MeOH |
| Amount (mL) | 20 | 15 | 15 | 15 |
| Acid/Cr | 0.058 | 0.082 | 0.038 | 0.007 |
| Alcohol/Cr | | | | 0.198 |
| GC-MS/Cr | 0.426 | 0.153 | 0.095 | 0.458 |
| Total/Cr | 0.426 | 0.235 | 0.133 | 0.663 |
| Oxygenated Products | 1-hexene-3-ol | 19% formic acid | 35% formic acid | 28% ethanol 22% |
| | hexanoic acid | 14% 1-hexen-3-ol | 18% 1-hexen-3-ol | 24% 2-hexen-1-ol 15% |
| | 1,2-hexanediol | 14% 1,2-hexanediol | 12% 1,2-hexanediol | 18% 1-hexen-3-ol 13% |
| | C6 oxygenate | 10% C6H14O2—Si | 8% C6H12O | 9% 3-hexanone 11% |
| | formic acid | 9% 2-hexenal | 6% 2-hexenal | 9% 2-hexenal 10% |
| | 2-hexen-1-ol | 7% dimethylbutanol | 4% 2-hexen-1-ol | 7% 2-hexanol 9% |
| | C5/C6 oxygenate | 6% 2-hexene-1-ol | 4% 2-hexanol | 5% n-propanol 7% |
| | acetic acid | 5% 2-octanone | 3% | 2-hexanone 6% |
| | | 2-hexanone | 2% | 1,2-hexanediol 5% |
| | | hexanal | 2% | |
| | | C6H12O | 2% | |
| | | 2-hexanol | 2% | |

| Example | 53 | 54 | 55 | 56 |
|---|---|---|---|---|
| Catalyst | E | D | D | D |
| Weight (g) | 2.0 | 1.6 | 2.2 | 2.0 |
| Reductant | 1-Hexene | 1-Hexene | 1-Hexene | 1-Hexene |
| Amount | 0.5 mL | 0.5 mL | 0.5 mL | 0.5 mL |
| Light | 24 hr UV | 2 hr UV | Dark—24 hr | 24 hr UV |
| Color | | Blue-gray | | Magenta |
| Hydrolysis | $H_2O + CH_3CN$ | $H_2O$ | $H_2O$ | $H_2O$ |
| Amount (mL) | 15 | 10 | 15 | 15 |
| Acid/Cr | 0.127 | 0.011 | 0.011 | 0.011 |
| Alcohol/Cr | 0.069 | 0.021 | 0.010 | 0.013 |
| GC-MS/Cr | 0.012 | 0.040 | 0.163 | 0.134 |
| Total/Cr | 0.208 | 0.072 | 0.184 | 0.159 |
| Oxygenated Products | acetic acid | 58% 1,2-hexanediol | 26% 1-hexen-3-ol | 28% 1-hexen-3-ol 19% |
| | methanol | 13% formic acid | 15% 2-hexenal | 17% 1,2-hexanediol 15% |
| | ethanol | 10% ethanol | 14% 1,2-hexanediol | 13% 2-hexenal 12% |
| | 1-butanol | 7% isobutanol | 12% C6H12O | 8% 2-hexanone 9% |
| | 1,2-hexanediol | 6% C6H14O | 7% C6H12O | 7% 2-hexen-1-ol 6% |
| | formic acid | 4% C9/C10 oxygenate | 6% 2-hexen-1-ol | 6% formic acid 6% |
| | n-propanol | 3% 1-hexanol | 3% formic acid | 5% C6H12O 5% |
| | | 1-butanol | 3% dimethylbutanoic | 5% C6H12O2 4% |
| | | 1-pentanol | 2% acid | hexenal 4% |
| | | 2-hexanone | 2% 1-butanol | 3% 1-butanol 4% |
| | | | 3-Me-2-pentanone | 2% C6H14O 3% |
| | | | | 2-hexanol 3% |

| Example | 57 | 58 | 59 | 60 |
|---|---|---|---|---|
| Catalyst | D | J | F | H1 |
| Weight (g) | 2.0 | 2.6 | 2.8 | 1.9 |
| Reductant | 1-Hexene | 1-Hexene | 1-Hexene | 1-Hexene |
| Amount | 0.5 mL | 0.5 mL | 0.5 mL | 0.5 mL |
| Light | 2 hr UV | 31 hr Blue | 31 hr Blue | 40 hr Blue |
| Color | Sky blue | Dark red | Blue-gray-black | Green-brown |
| Hydrolysis | $H_2O$ | $H_2O + CH_3CN$ | $H_2O + CH_3CN$ | $H_2O + CH_3CN$ |
| Amount (mL) | 15 | 15 | 15 | 15 |

TABLE 1-continued

Summary of Examples 1-67 (products in mol %)

| | | | | | | | | |
|---|---|---|---|---|---|---|---|---|
| Acid/Cr | 0.012 | | 0.010 | | 0.001 | | 0.003 | |
| Alcohol/Cr | 0.014 | | | | | | | |
| GC-MS/Cr | 0.102 | | 0.496 | | 0.794 | | 0.155 | |
| Total/Cr | 0.127 | | 0.506 | | 0.795 | | 0.158 | |
| Oxygenated Products | 1-hexen-3-ol | 23% | 1,2-hexanediol | 37% | 1,2-hexanediol | 20% | 3,4-hexandiol | 9% |
| | 2-hexenal | 15% | 1-hexen-3-ol | 14% | 1-hexen-3-one | 20% | C6H10O ketone | 9% |
| | 1,2-hexandiol | 10% | 5-hexen-2-ol | 14% | 2-hexenal | 13% | 2-hexanol | 9% |
| | formic acid | 8% | 5-hexen-3-ol | 11% | butanoic acid ethyl ester | 11% | C6H12O alcohol | 8% |
| | C6H12O | 7% | ethyl butanoate | 5% | | | 1-hexen-3-ol | 8% |
| | C6H12O | 7% | 1-pentanol | 4% | 2-hexen-1-ol | 7% | 2,3 hexanediol | 7% |
| | 2-hexen-1-ol | 4% | 2-hexen-1-ol | 4% | 2-hexanone | 4% | C6H12O alcohol | 7% |
| | 1-butanol | 4% | 5-hexen-1-ol | 4% | 1-hexen-3-ol | 3% | C6H10O ketone | 5% |
| | diMe butanoic acid | 4% | C6H12O | 2% | C6H12O alcohol | 3% | 2-hexanone | 5% |
| | isobutanol | 3% | C6H12O | 1% | hexanediol | 3% | 2-hexenal | 4% |
| | 2-hexen-1-ol | 2% | 2-hexenal | 1% | 2-hexen-1-ol | 3% | 1,2-hexanediol | 2% |
| | | | | | 3-hexen-2-one | 3% | | |

| Example | 61 | | 62 | | 63 | | 64 | |
|---|---|---|---|---|---|---|---|---|
| Catalyst | G1 | | K | | L | | D | |
| Weight (g) | 2.1 | | 2.9 | | 2.7 | | 1.9 | |
| Reductant | 1-Hexene | | 1-Hexene | | 1-Hexene | | 2-Hexene | |
| Amount | 0.5 mL | | 2 mL | | 2 mL | | 0.5 mL | |
| Light | 40 hr Blue | | UV 24 h | | UV 24 h | | 14 hr Blue | |
| Color | Green-brown | | Brown | | Brown | | Blue-gray | |
| Hydrolysis | $H_2O + CH_3CN$ | | 4% $H_2O$/MeOH | | 4% $H_2O$/MeOH | | $H_2O$ | |
| Amount (mL) | 15 | | 15 | | 15 | | 20 | |
| Acid/Cr | 0.012 | | 0.003 | | 0.003 | | 0.145 | |
| Alcohol/Cr | | | 0.003 | | 0.004 | | | |
| GC-MS/Cr | 0.147 | | 0.025 | | 0.051 | | 2.318 | |
| Total/Cr | 0.159 | | 0.031 | | 0.058 | | 2.462 | |
| Oxygenated Products | 1-hexen-3-ol | 18% | 5-hexen-2-ol | 21% | 5-hexen-2-ol | 17% | 2,3-hexanediol | 21% |
| | C6H12O | 10% | 5-hexen-2-one | 16% | 5-hexene-ol | 13% | 3-hexen-2-one | 17% |
| | 1,2-hexanediol | 9% | 5-hexen-3-ol | 15% | 1-hexen-3-ol | 10% | 4-hexen-3-one | 11% |
| | C6H12O | 8% | 1-hexen-3-ol | 7% | 5-hexen-2-one | 9% | 3,4-hexandiol | 8% |
| | 2-hexanol | 8% | isopropanol | 7% | 1-pentanol | 6% | 4-hexen-3-ol | 8% |
| | C6H12O | 7% | formic acid | 7% | C11/12 oxygenate | 4% | 2-Me-1-penten-3-ol | 8% |
| | C6H14O2 | 7% | 1-pentanol | 7% | formic acid | 4% | 1-hexen-3-ol | 5% |
| | 2,3-hexanediol | 5% | 5-hexene-ol | 7% | isopropanol | 4% | 2-hexenal | 3% |
| | C6H12O | 4% | 4-hexen-3-one | 4% | 5-hexen-1-ol | 3% | formic acid | 3% |
| | acetic acid | 3% | ethanol | 3% | C10-12 oxygenate | 3% | C6H12O | 2% |
| | 2-hexen-1-ol | 3% | 2-hexenal | 3% | 1,2-hexanediol | 3% | 2-butenal | 2% |
| | formic acid | 3% | | | pentanal | 3% | 4-hexen-1-ol | 2% |

| Example | 65 | | 66 | | 67 | | | |
|---|---|---|---|---|---|---|---|---|
| Catalyst | D | | D | | D | | | |
| Weight (g) | 2.3 | | 2.2 | | 2.0 | | | |
| Reductant | n-Pentane | | n-Pentane | | n-Pentane | | | |
| Amount | 0.25 mL | | 1 mL | | 3 mL | | | |
| Light | UV 24 hr | | UV 24 hr | | UV 24 hr | | | |
| Color | Dark blue-gray | | Green | | Dark blue-gray | | | |
| Hydrolysis | 5% $H_2O$/MeOH | | 5% $H_2O$/MeOH | | 5% $H_2O$/MeOH | | | |
| Amount (mL) | 15 | | 15 | | 15 | | | |
| Acid/Cr | 0.013 | | 0.011 | | 0.012 | | | |
| Alcohol/Cr | | | | | | | | |
| GC-MS/Cr | 0.323 | | 1.819 | | 1.074 | | | |
| Total/Cr | 0.336 | | 1.831 | | 1.086 | | | |
| Oxygenated Products | 2-pentanol | 46% | 2-pentanol | 39% | 2-pentanol | 62% | | |
| | 1-pentanol | 21% | 1-pentanol | 16% | 2-pentanone | 18% | | |
| | 2-pentanone | 13% | 2-pentanone | 13% | 3-pentanone | 9% | | |
| | 3-pentanone | 6% | 3-pentanone | 6% | 1-pentanol | 3% | | |
| | 2-hexenal | 5% | C5H10O | 4% | 2-pentenal | 2% | | |
| | formic acid | 3% | C10H18O | 2% | 3-penten-2-one | 2% | | |
| | 2-pentenal | 2% | C7H12O | 2% | C7H12O | 2% | | |
| | 2-Me-2-butenal | 2% | C8H14O | 1% | formic acid | 1% | | |

Examples 68-74

Examples 68-74 were performed to determine the extent of reduction of the hexavalent chromium and the average valence after reduction in a representative supported chromium catalyst. Table II summarizes the results. Example 74 was a chromium/silica-titania catalyst containing approximately 0.8 wt. % chromium and 7 wt. % titania, and having a BET surface area of 530 m²/g, a pore volume of 2.6 mL/g, and an average particle size of 130 um, which was calcined in dry air at 850° C. for 3 hr to convert chromium to the hexavalent oxidation state (orange). This converted over 86 wt. % of the chromium into the hexavalent state. For Examples 68-69, approximate 2 g samples of the catalyst of Example 74 were separately charged to a glass reaction vessel and 0.5 mL of liquid isopentane was charged to the vessel. For Examples 70-71, about 1.5 atm of gaseous ethane was charged to the glass bottle. Then, the bottle was placed in a light-proof box under blue fluorescent light (approximately 2 times the intensity expected from sunlight), and the bottle was continuously rotated so that all of the catalyst was exposed to the light for 24 hr. The final catalyst color is noted in Table II. Afterward, into the bottle, along with the catalyst, was introduced about 20 mL of a solution of 2 M $H_2SO_4$. To this was added 5 drops of ferroin Fe(+3) indicator. This usually turned a blue-green color indicating the presence of Fe(III) ions. Next, the solution was titrated to the ferroin endpoint (red color) using a solution of ferrous ammonium sulfate, which had been previously calibrated by reaction with a standardized 0.1 M sodium dichromate solution. When the solution turned red, the end point was signaled, and the titrant volume was recorded, to calculate the oxidation capacity of the catalyst, expressed as wt. % Cr(VI) and as percent reduced, that is, the percent of the original Cr(VI) oxidative power that has been removed by the reduction treatment. The average valence was also computed by multiplying the percent reduced by +3 and subtracting that number from +6.

Of course, this treatment gives only an average oxidation state. Note that although Table II lists the oxidative power measured as wt. % Cr(VI), in reality all of the chromium could be present in lower valence states, such as Cr(IV) or Cr(V). Thus, the Cr(VI) value in Table II only lists the maximum amount of Cr(VI) that could be present. More likely, the reduced chromium catalysts have a combination of several valence states that produce the measured oxidative power. Note that some of the reduced chromium, and particularly those catalysts reduced with CO, may be in the divalent state, which would not have been detected in this test, which stops in the trivalent state.

Example 74 demonstrates that the air-calcined chromium catalyst contained substantially most of its chromium (0.69/0.80=86 wt. %) present as Cr(VI), and it is this Cr(VI) amount that is being reduced in the light treatment. Therefore, this amount of Cr(VI) serves as the starting amount, which had an average valence of +6, and which serves as a reference, to which the reduced catalysts are then compared. Examples 68-69 were reduced chromium catalysts with an average valence of approximately +3.3, with no more than 0.06 wt. % Cr(VI), and with less than 10 wt. % of the starting hexavalent chromium still remaining in the hexavalent oxidation state. Examples 70-71 were reduced chromium catalysts with an average valence of approximately +4.1, with no more than 0.26 wt. % Cr(VI), and with less than 40 wt. % of the chromium in the hexavalent oxidation state. For Examples 72-73, the supported chromium catalyst was reduced in CO with either blue light or elevated temperature, resulting in no oxidative power being measured (0 wt. % Cr(VI) in the table). Thus, the average valence must be no more than +3. But the supported chromium catalyst that was CO-reduced by conventional means (Example 73) is known to have a valence of mostly Cr(II) after reduction, which is not detected in this test. Accordingly, Examples 72 and 73 are listed as less than or equal to +3. Notably, this test cannot distinguish between Cr(II) and Cr(III) species, but there was no measurable amount of hexavalent chromium in Examples 72-73.

TABLE II

Examples 68-74

| Example | Reductant | Treatment | Color | Catalyst (g) | Cr(VI) (wt. %) | Reduced (wt. %) | Average Valence |
|---|---|---|---|---|---|---|---|
| 68 | isopentane | Blue light 24 hr | blue | 2.05 | 0.06 | 90.8 | 3.28 |
| 69 | isopentane | Blue light 24 hr | blue | 2.08 | 0.06 | 90.9 | 3.27 |
| 70 | ethane | Blue light 24 hr | olive green | 2.14 | 0.26 | 62.3 | 4.13 |
| 71 | ethane | Blue light 24 hr | olive green | 2.30 | 0.26 | 61.9 | 4.14 |
| 72 | CO | Blue light 2 hr | blue green | 2.33 | 0.00 | 100 | <3 |
| 73 | CO | CO reduction 30 min—350° C. | blue | 2.52 | 0.00 | 100 | <3 |
| 74 | None | None | orange | — | 0.69 | 0 | 6.00 |

The invention is described above with reference to numerous aspects and specific examples. Many variations will suggest themselves to those skilled in the art in light of the above detailed description. All such obvious variations are within the full intended scope of the appended claims. Other aspects of the invention can include, but are not limited to, the following (aspects are described as "comprising" but, alternatively, can "consist essentially of" or "consist of"):

Aspect 1. A process for converting a hydrocarbon reactant into an alcohol compound and/or a carbonyl compound, the process comprising:
(a)(i) heat treating a supported chromium precursor at a peak temperature from about 50° C. to about 1000° C. to form a supported chromium catalyst comprising chromium in a hexavalent oxidation state; or
(a)(ii) contacting a chromium precursor with a solid support while heat treating at a peak temperature from about 50° C. to about 1000° C. to form a supported chromium catalyst comprising chromium in a hexavalent oxidation state; or
(a)(iii) heat treating a solid support at a peak temperature from about 50° C. to about 1000° C. and then contacting a chromium precursor with the solid support to form a supported chromium catalyst comprising chromium in a hexavalent oxidation state;
(b) irradiating the hydrocarbon reactant and the supported chromium catalyst with a light beam at a wavelength in the UV-visible spectrum to reduce at least a portion of the supported chromium catalyst to form a reduced chromium catalyst (e.g., at least a portion of the chromium on the reduced chromium catalyst can have at least one bonding site with a hydrocarboxy group (—O-hydrocarbon group)); and (c) hydrolyzing the reduced chromium catalyst to form a reaction product comprising the alcohol compound and/or the carbonyl compound.

Aspect 2. The process defined in aspect 1, wherein the hydrocarbon reactant comprises a saturated or an unsaturated, linear or branched, aliphatic hydrocarbon, and including combinations thereof.

Aspect 3. The process defined in aspect 1, wherein the hydrocarbon reactant comprises an aromatic compound (e.g., benzene, toluene, xylene, and substituted versions thereof, and including combinations thereof).

Aspect 4. The process defined in aspect 1, wherein the hydrocarbon reactant comprises a linear alkane compound, a branched alkane compound, a cyclic alkane compound, or a combination thereof.

Aspect 5. The process defined in aspect 1, wherein the hydrocarbon reactant comprises a linear olefin compound (e.g., an α-olefin), a branched olefin compound, a cyclic olefin compound, or a combination thereof.

Aspect 6. The process defined in aspect 1, wherein the hydrocarbon reactant comprises any suitable carbon number alkane compound or any carbon number alkane compound disclosed herein, e.g., a $C_1$ to $C_{36}$ alkane compound, a $C_1$ to $C_{18}$ alkane compound, a $C_1$ to $C_{12}$ alkane compound, or a $C_1$ to $C_8$ alkane compound; and/or the hydrocarbon reactant comprises any suitable carbon number olefin compound or any carbon number olefin compound disclosed herein, e.g., a $C_2$ to $C_{36}$ olefin compound, a $C_2$ to $C_{18}$ olefin compound, a $C_2$ to $C_{12}$ olefin compound, or a $C_2$ to $C_8$ olefin compound; and/or the hydrocarbon reactant comprises any suitable carbon number aromatic compound or any carbon number aromatic compound disclosed herein, e.g., a $C_6$ to $C_{36}$ aromatic compound, a $C_6$ to $C_{18}$ aromatic compound, a $C_6$ to $C_{12}$ aromatic compound, or a $C_6$ to $C_8$ aromatic compound.

Aspect 7. The process defined in aspect 1, wherein the hydrocarbon reactant comprises methane, ethane, propane, butane (e.g., n-butane or isobutane), pentane (e.g., n-pentane, neopentane, or isopentane), hexane, heptane, octane, nonane, decane, undecane, dodecane, tridecane, tetradecane, pentadecane, hexadecane, heptadecane, octadecane, or any combination thereof, or the hydrocarbon reactant comprises methane, ethane, propane, n-butane, isobutane, n-pentane, neopentane, isopentane, n-hexane, n-heptane, n-octane, n-decane, n-dodecane, or any combination thereof, or the hydrocarbon reactant comprises methane, ethane, propane, butane, pentane, hexane, or any combination thereof.

Aspect 8. The process defined in aspect 1, wherein the hydrocarbon reactant comprises ethylene, propylene, 1-butene, 1-pentene, 1-hexene, 1-heptene, 1-octene, 1-decene, 1-dodecene, 1-tetradecene, 1-hexadecene, 1-octadecene, cyclopentene, cyclohexene, or any combination thereof.

Aspect 9. The process defined in aspect 1, wherein the hydrocarbon reactant comprises benzene, toluene, ethylbenzene, xylene, mesitylene, or any combination thereof.

Aspect 10. The process defined in aspect 1, wherein the hydrocarbon reactant comprises a $C_n$ hydrocarbon compound, the alcohol compound comprises a $C_n$ alcohol compound, and the carbonyl compound comprises a $C_n$ carbonyl compound.

Aspect 11. The process defined in aspect 10, wherein n is any suitable integer or an integer in any range disclosed herein, e.g., from 1 to 36, from 1 to 18, from 1 to 12, or from 1 to 8.

Aspect 12. The process defined in aspect 1, wherein the hydrocarbon reactant comprises methane, and the alcohol compound comprises methanol.

Aspect 13. The process defined in any one of the preceding aspects, wherein the supported chromium catalyst and the reduced chromium catalyst comprise any suitable amount of chromium or an amount in any range disclosed herein, e.g., from about 0.01 to about 50 wt. %, from about 0.01 to about 10 wt. %, from about 0.1 to about 15 wt. %, from about 0.1 to about 0.5 wt. %, from about 0.2 to about 10 wt. %, from about 0.5 to about 2.5 wt. %, from about 2 to about 30 wt. %, or from about 3 to about 15 wt. % of chromium, based on the weight of the supported chromium catalyst or the reduced chromium catalyst.

Aspect 14. The process defined in any one of the preceding aspects, wherein the reduced chromium catalyst comprises any suitable amount of chromium in an average oxidation state of +5 or less, or an amount in any range disclosed herein, e.g., from about 0.01 to about 50 wt. %, from about 0.01 to about 10 wt. %, from about 0.1 to about 15 wt. %, from about 0.1 to about 0.5 wt. %, from about 0.2 to about 10 wt. %, from about 0.5 to about 2.5 wt. %, from about 2 to about 30 wt. %, or from about 3 to about 15 wt. % of chromium in an average oxidation state of +5 or less, based on the weight of the reduced chromium catalyst.

Aspect 15. The process defined in any one of the preceding aspects, wherein the amount of the chromium of the supported chromium catalyst in a hexavalent oxidation state is at least about 10 wt. %, at least about 20 wt. %, at least about 40 wt. %, at least about 60 wt. %, at least about 80 wt. %, or at least about 90 wt. %, based on the total amount of chromium on the supported chromium catalyst, and/or the amount of chromium of the reduced chromium catalyst in a hexavalent oxidation state is (from 0 wt. %, from about 0.5 wt. %, from about 1 wt. %, or from about 2 wt. % to) less than or equal to about 50 wt. %, less than or equal to about 40 wt. %, less than or equal to about 30 wt. %, or less than or equal to about 15 wt. %, based on the total amount of chromium on the reduced chromium catalyst.

Aspect 16. The process defined in any one of the preceding aspects, wherein at least about 10 wt. %, at least about 20 wt. %, at least about 40 wt. %, at least about 60 wt. %, at least about 80 wt. %, or at least about 90 wt. %, of the supported chromium catalyst is reduced to form the reduced chromium catalyst, based on the total amount of the supported chromium catalyst.

Aspect 17. The process defined in any one of the preceding aspects, wherein the chromium in the reduced chromium catalyst has an average valence of less than or equal to about 5.25, less than or equal to about 5, less than or equal to about 4.75, less than or equal to about 4.5, less than or equal to about 4.25, or less than or equal to about 4.

Aspect 18. The process defined in any one of aspects 1-17, wherein the supported chromium precursor, the solid support, the supported chromium catalyst, and the reduced chromium catalyst comprise any suitable solid oxide or any solid oxide disclosed herein, e.g., silica, alumina, silica-alumina, silica-coated alumina, aluminum phosphate, aluminophosphate, heteropolytungstate, titania, zirconia, magnesia, boria, zinc oxide, silica-titania, silica-zirconia, alumina-titania, alumina-zirconia, zinc-aluminate, alumina-boria, alumina borate, silica-boria, aluminophosphate-silica, titania-zirconia, or any combination thereof.

Aspect 19. The process defined in any one of aspects 1-17, wherein the supported chromium precursor, the solid support, the supported chromium catalyst, and the reduced chromium catalyst comprise silica, silica-alumina, silica-coated alumina, silica-titania, silica-titania-magnesia, silica-zirconia, silica-magnesia, silica-boria, aluminophosphate-silica, alumina, alumina borate, or any combination thereof.

Aspect 20. The process defined in any one of aspects 1-17, wherein the supported chromium precursor, the solid support, the supported chromium catalyst, and the reduced chromium catalyst comprise a chemically-treated solid oxide comprising a solid oxide (e.g., as in aspect 18 or 19, such as silica, alumina, silica-alumina, silica-titania, silica-zirconia, silica-yttria, aluminophosphate, zirconia, titania, thoria, or stania) treated with an electron-withdrawing anion.

Aspect 21. The process defined in aspect 20, wherein the electron-withdrawing anion comprises sulfate, bisulfate, fluoride, chloride, bromide, iodide, fluorosulfate, fluoroborate, phosphate, fluorophosphate, trifluoroacetate, triflate, fluorozirconate, fluorotitanate, phosphotungstate, tungstate, molybdate, or any combination thereof.

Aspect 22. The process defined in aspect 20 or 21, wherein the chemically-treated solid oxide contains from about 1 to about 30 wt. %, from about 2 to about 20 wt. %, from about 2 to about 15 wt. %, from about 3 to about 12 wt. %, or from 4 to 10 wt. %, of the electron-withdrawing anion, based on the total weight of the chemically-treated solid oxide.

Aspect 23. The process defined in any one of aspects 1-17, wherein the supported chromium precursor, the solid support, the supported chromium catalyst, and the reduced chromium catalyst comprise a chemically-treated solid oxide comprising fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, fluorided-chlorided silica-coated alumina, sulfated silica-coated alumina, phosphated silica-coated alumina, or any combination thereof.

Aspect 24. The process defined in any one of aspects 1-17, wherein the supported chromium precursor, the supported chromium catalyst, and the reduced chromium catalyst comprise chromium/silica, chromium/silica-titania, chromium/silica-titania-magnesia, chromium/silica-alumina, chromium/silica-coated alumina, chromium/aluminophosphate, chromium/alumina, chromium/alumina borate, or any combination thereof.

Aspect 25. The process defined in any one of aspects 1-17, wherein the supported chromium precursor, the supported chromium catalyst, and the reduced chromium catalyst comprise chromium/silica-titania, and the supported chromium precursor, the supported chromium catalyst, and the reduced chromium catalyst comprise any suitable amount of titanium or an amount in any range disclosed herein, e.g., from about 0.1 to about 20 wt. %, from about 0.5 to about 15 wt. %, from about 1 to about 10 wt. %, or from about 1 to about 6 wt. %, based on the weight of the respective supported chromium precursor, supported chromium catalyst, and reduced chromium catalyst.

Aspect 26. The process defined in any one of aspects 1-17, wherein the supported chromium precursor, the supported chromium catalyst, and the reduced chromium catalyst comprise chromium/sulfated alumina, chromium/fluorided alumina, chromium/fluorided silica-alumina, chromium/fluorided silica-coated alumina, or any combination thereof.

Aspect 27. The process defined in any one of aspects 1-17, wherein the supported chromium precursor, the solid support, the supported chromium catalyst, and the reduced chromium catalyst comprise a zeolite.

Aspect 28. The process defined in aspect 27, wherein the supported chromium precursor, the solid support, the supported chromium catalyst, and the reduced chromium catalyst comprise a medium pore zeolite, a large pore zeolite, or a combination thereof.

Aspect 29. The process defined in aspect 27, wherein the zeolite comprises a ZSM-5 zeolite, a ZSM-11 zeolite, an EU-1 zeolite, a ZSM-23 zeolite, a ZSM-57 zeolite, an ALPO4-11 zeolite, an ALPO4-41 zeolite, a Ferrierite framework type zeolite, or a combination thereof.

Aspect 30. The process defined in aspect 27, wherein the supported chromium precursor, the solid support, the supported chromium catalyst, and the reduced chromium catalyst comprise an L-zeolite, a Y-zeolite, a mordenite, an omega zeolite, and/or a beta zeolite.

Aspect 31. The process defined in any one of aspects 27-30, wherein the supported chromium precursor, the solid support, the supported chromium catalyst, and the reduced chromium catalyst comprise the zeolite and any suitable amount of binder or an amount in any range disclosed herein, e.g., from about 3 wt. % to about 35 wt. %, or from about 5 wt. % to about 30 wt. % binder, based on the weight of the respective supported chromium precursor, solid support, supported chromium catalyst, and reduced chromium catalyst.

Aspect 32. The process defined in any one of aspects 1-17, wherein the supported chromium precursor, the solid support, the supported chromium catalyst, and the reduced chromium catalyst comprise a clay, an activated carbon, or a combination thereof.

Aspect 33. The process defined in any one of the preceding aspects, wherein the supported chromium precursor, the solid support, the supported chromium catalyst, and the reduced chromium catalyst have any suitable pore volume (total) or a pore volume (total) in any range disclosed herein, e.g., from about 0.1 to about 5 mL/g, from about 0.15 to about 5 mL/g, from about 0.1 to about 3 mL/g, or from about 0.1 to about 0.8 mL/g.

Aspect 34. The process defined in any one of the preceding aspects, wherein the supported chromium precursor, the solid support, the supported chromium catalyst, and the reduced chromium catalyst have any suitable BET surface area or a BET surface area in any range disclosed herein, e.g., from about 50 to about 2000 $m^2/g$, from about 50 to about 700 $m^2/g$, from about 50 to about 400 $m^2/g$, from about 600 to about 1200 $m^2/g$, or from about 150 to about 525 $m^2/g$.

Aspect 35. The process defined in any one of the preceding aspects, wherein the supported chromium precursor, the solid support, the supported chromium catalyst, and the reduced chromium catalyst are in any suitable shape or form or any shape or form disclosed herein, e.g., powder, round or spherical (e.g., spheres), ellipsoidal, pellet, bead, cylinder, granule (e.g., regular and/or irregular), trilobe, quadralobe, ring, wagon-wheel, monolith, or any combination thereof.

Aspect 36. The process defined in any one aspects 1-35, wherein the supported chromium precursor, the solid support, the supported chromium catalyst, and the reduced chromium catalyst have any suitable average (d50) particle size or an average (d50) particle size in any range disclosed herein, e.g., from about 10 to about 500 microns, from about 25 to about 250 microns, or from about 20 to about 100 microns.

Aspect 37. The process defined in any one aspects 1-35, wherein the supported chromium precursor, the solid support, the supported chromium catalyst, and the reduced chromium catalyst comprise pellets or beads having any suitable average size or an average size in any range disclosed herein, e.g., from about 1/16 inch to about 1/2 inch, or from about 1/8 inch to about 1/4 inch.

Aspect 38. The process defined in any one of aspects 1-37, wherein the wavelength comprises a single wavelength or a range of wavelengths in the visible spectrum (from 380 nm to 780 nm).

Aspect 39. The process defined in any one of aspects 1-37, wherein the wavelength comprises a single wavelength or a range of wavelengths in the 200 nm to 750 nm range.

Aspect 40. The process defined in any one of aspects 1-37, wherein the wavelength comprises a single wavelength or a range of wavelengths in the 300 to 750 nm range, the 350 nm to 650 nm range, the 300 nm to 500 nm range, or the 300 nm to 400 nm range.

Aspect 41. The process defined in any one of aspects 1-37, wherein the wavelength comprises a single wavelength or a range of wavelengths below 600 nm, below 525 nm, or below 500 nm.

Aspect 42. The process defined in any one of aspects 1-41, wherein the wavelength is a single wavelength.

Aspect 43. The process defined in any one of aspects 1-41, wherein the wavelength is a range of wavelengths spanning at least 25 nm, at least 50 nm, at least 100 nm, or at least 200 nm.

Aspect 44. The process defined in any one of the preceding aspects, wherein the light beam has any suitable intensity or an intensity in any range disclosed herein, e.g., at least about 500 lumens, at least about 1000 lumens, at least about 2000 lumens, at least about 5000 lumens, at least about 10,000 lumens, or at least about 20,000 lumens.

Aspect 45. The process defined in any one of the preceding aspects, wherein the light beam has any suitable power or any power disclosed herein, e.g., at least about 50 watts, at least about 100 watts, at least about 200 watts, at least about 500 watts, at least about 1,000 watts, or at least about 2,000 watts.

Aspect 46. The process defined in any one of the preceding aspects, wherein the supported chromium catalyst is irradiated with any suitable illuminance or any illuminance disclosed herein, e.g., at least about 100 lux, at least about 500 lux, at least about 1000 lux, at least about 2000 lux, at least about 5000 lux, at least about 10,000 lux, at least about 20,000 lux, or at least about 100,000 lux.

Aspect 47. The process defined in any one of the preceding aspects, wherein the irradiating step is conducted at any suitable temperature or any temperature disclosed herein, e.g., less than about 200° C., less than about 100° C., less than about 40° C., from about −100° C. to about 100° C., from about 0° C. to about 100° C., or from about 10° C. to about 40° C.

Aspect 48. The process defined in any one of the preceding aspects, wherein the irradiating step is conducted for any suitable exposure time or for any exposure time disclosed herein, e.g., from about 15 sec to about 48 hr, from about 1 min to about 6 hr, from about 1 min to about 15 min, or from about 1 hr to about 8 hr.

Aspect 49. The process defined in any one of the preceding aspects, wherein the molar ratio of the hydrocarbon reactant to chromium (of the supported chromium catalyst) is in any suitable range or any range disclosed herein, e.g., at least about 0.25:1, at least about 0.5:1, at least about 1:1, at least about 10:1, at least about 100:1, at least about 1000:1, or at least about 10,000:1.

Aspect 50. The process defined in any one of aspects 1-49, wherein the hydrocarbon reactant is in a gas phase during the irradiating step.

Aspect 51. The process defined in any one of aspects 1-49, wherein the hydrocarbon reactant is in a liquid phase during the irradiating step.

Aspect 52. The process defined in any one of aspects 1-49, wherein the process comprises irradiating a slurry of the supported chromium catalyst in the hydrocarbon reactant.

Aspect 53. The process defined in any one of aspects 1-49, wherein the process comprises contacting the hydrocarbon reactant with a fluidized bed of the supported chromium catalyst, and irradiating while contacting (fluidizing).

Aspect 54. The process defined in any one of aspects 1-49, wherein the process comprises contacting the hydrocarbon reactant (e.g., in a gas phase or in a liquid phase) with a fixed bed of the supported chromium catalyst, and irradiating while contacting.

Aspect 55. The process defined in any one of the preceding aspects, wherein the step of irradiating the hydrocarbon reactant with the supported chromium catalyst is conducted at any suitable WHSV or a WHSV in any range disclosed herein, e.g., from about 0.01 $hr^{-1}$ to about 500 $hr^{-1}$, or from about 0.1 $hr^{-1}$ to about 10 $hr^{-1}$.

Aspect 56. The process defined in any one of the preceding aspects, wherein the hydrolyzing step is conducted at any suitable temperature or any temperature disclosed herein, e.g., less than about 200° C., less than about 100° C., less than about 40° C., from about 0° C. to about 100° C., or from about 10° C. to about 40° C.

Aspect 57. The process defined in any one of the preceding aspects, wherein the hydrolyzing step comprises contacting the reduced chromium catalyst with a hydrolysis agent.

Aspect 58. The process defined in aspect 57, wherein the hydrolysis agent comprises any suitable hydrolysis agent or any hydrolysis agent disclosed herein, e.g., water, steam, an alcohol agent, an acid agent, an alkaline agent, or any combination thereof.

Aspect 59. The process defined in aspect 58, wherein the hydrolysis agent further comprises any suitable reducing agent or any reducing agent disclosed herein, e.g., ascorbic acid, an iron (II) reducing agent, a zinc reducing agent, or any combination thereof.

Aspect 60. The process defined in any one of the preceding aspects, wherein the carbonyl compound comprises an aldehyde compound, a ketone compound, an organic acid compound, or any combination thereof.

Aspect 61. The process defined in any one of the preceding aspects, wherein a conversion of the hydrocarbon reactant (or a yield to the alcohol compound, or a yield to the carbonyl compound) is any percent conversion (or yield) disclosed herein, e.g., at least about 2 wt. %, at least about 5 wt. %, at least about 10 wt. %, or at least about 15 wt. % (and up to about 99 wt. %, about 95 wt. %, about 90 wt. %, about 80 wt. %, about 70 wt. %, or about 50 wt. %).

Aspect 62. The process defined in any one of the preceding aspects, wherein a single pass conversion of the hydrocarbon reactant (or a single pass yield to the alcohol compound, or a single pass yield to the carbonyl compound) is any single pass percent conversion (or single pass yield) disclosed herein, e.g., at least about 2 wt. %, at least about 5 wt. %, at least about 10 wt. %, or at least about 15 wt. % (and up to about 99 wt. %, about 95 wt. %, about 90 wt. %, about 80 wt. %, about 70 wt. %, or about 50 wt. %).

Aspect 63. The process defined in any one of the preceding aspects, wherein the yield to the alcohol compound (or the carbonyl compound) per mole of chromium (VI) in the supported chromium catalyst is any molar ratio based on moles of chromium (VI) disclosed herein, e.g., at least about 0.01, at least about 0.05, at least about 0.1, or at least about 0.25 moles (and up to 2, up to about 1.8, up to about 1.6, up to about 1.4, up to about 1.2, or up to about 1 mole) of the alcohol compound (or the carbonyl compound).

Aspect 64. The process defined in any one of the preceding aspects, further comprising a step of separating at least a portion (and in some cases, all) of the hydrocarbon reactant from the reaction product after step (c) to produce a separated hydrocarbon portion using any suitable technique or any technique disclosed herein, e.g., extraction, filtration, evaporation, distillation, or any combination thereof.

Aspect 65. The process defined in aspect 64, wherein the separated hydrocarbon portion is recycled and irradiated with the supported chromium catalyst again.

Aspect 66. The process defined in any one of the preceding aspects, further comprising a step of separating at least a portion (and in some cases, all) of the alcohol compound and/or the carbonyl compound from the reaction product using any suitable technique or any technique disclosed herein, e.g., extraction, filtration, evaporation, distillation, or any combination thereof.

Aspect 67. The process defined in any one of the preceding aspects, further comprising a step of separating at least a portion (and in some cases, all) of the reduced chromium catalyst from the reaction product after step (c) to produce a separated reduced chromium catalyst using any suitable technique or any technique disclosed herein, e.g., extraction, filtration, evaporation, distillation, or any combination thereof.

Aspect 68. The process defined in any one of the preceding aspects, further comprising a step of (d) calcining the reduced chromium catalyst or the separated reduced chromium catalyst to regenerate the supported chromium catalyst.

Aspect 69. The process defined in aspect 68, wherein calcining comprises subjecting the reduced chromium catalyst or the separated reduced chromium catalyst to an oxidizing atmosphere at any suitable calcining temperature and time conditions or any calcining temperature and time conditions disclosed herein, e.g., a calcining temperature from about 300° C. to about 1000° C., from about 500° C. to about 900° C., or from about 550° C. to about 870° C., for a time period of from about 1 min to about 24 hr, from about 1 hr to about 12 hr, or from about 30 min to about 8 hr.

Aspect 70. The process defined in any one of aspects 1-69, wherein the peak temperature in step (a)(i) and (a)(ii) and (a)(iii) is any suitable peak temperature or any peak temperature disclosed herein, e.g., from about 300° C. to about 1000° C., from about 400° C. to about 870° C., from about 300° C. to about 600° C., from about 100° C. to about 500° C., from about 50° C. to about 400° C., from about 100° C. to about 300° C., or from about 50° C. to about 200° C.

Aspect 71. The process defined in any one of aspects 1-70, wherein step (a)(i) and (a)(ii) and (a)(iii) are conducted in an oxidizing atmosphere.

Aspect 72. The process defined in any one of aspects 1-70, wherein step (a)(i) and (a)(ii) and (a)(iii) are conducted in an inert atmosphere.

Aspect 73. The process defined in any one of aspects 1-72, wherein the process comprises step (a)(i), and the supported chromium precursor comprises any suitable supported chromium precursor or any supported chromium precursor disclosed herein, e.g., $CrO_3$ (or anything calcinable to $CrO_3$), chromium (III) acetate, basic chromium (III) acetate, chromium (III) nitrate, chromium (III) sulfate, chromium (III) chloride (or bromide or iodide), chromium (II) chloride (or bromide or iodide), chromium (III) malate (or propionate, gluconate, or citrate), chromium (III) naphthenate, chromium (III) acetylacetonate (or other diketonate), chromyl chloride, chromium (III) methoxide (or ethoxide or other alkoxide), chromium (III) 2-ethyl hexanoate (or propionate or other carboxylate), a chromium (0) compound (e.g., chromium (0) hexacarbonyl, or a diarene chromium (0) compound such as bis-cumene chromium (0), bis-benzene chromium (0), or bis-toluene chromium (0)), a chromium (II) cyclopentadienyl-type compound (e.g., bis-cyclopentadienyl chromium (II) or bis-indenyl chromium (II)), a chromate compound (e.g., potassium chromate, sodium chromate, ammonium chromate, potassium dichromate, sodium dichromate, or ammonium dichromate), or any combination thereof.

Aspect 74. The process defined in any one of aspects 1-72, wherein the process comprises step (a)(i), and the supported chromium precursor comprises potassium chromate, sodium chromate, ammonium chromate, potassium dichromate, sodium dichromate, ammonium dichromate, or any combination thereof.

Aspect 75. The process defined in any one of aspects 1-72, wherein the process comprises step (a)(ii), and the chromium precursor comprises any suitable chromium precursor or any chromium precursor disclosed herein, e.g., chromium (III) acetylacetonate, chromium (0), chromyl chloride, chromic oxide ($Cr_2O_3$), $CrO_3$, chromium (III) sulfate, chromium (III) nitrate, a chromate compound (e.g., potassium chromate, sodium chromate, ammonium chromate, potassium dichromate, sodium dichromate, or ammonium dichromate), or any combination thereof.

Aspect 76. The process defined in any one of aspects 1-72, wherein the process comprises step (a)(ii), and the chromium precursor comprises potassium chromate, sodium chromate, ammonium chromate, potassium dichromate, sodium dichromate, ammonium dichromate, or any combination thereof.

Aspect 77. The process defined in any one of aspects 1-72, wherein the process comprises step (a)(iii), and the chromium precursor comprises any suitable chromium precursor or any chromium precursor disclosed herein, e.g., $CrO_3$, bis(t-butyl) chromate (or bis(triphenylsilyl) chromate, or other organic chromium (VI) ester), chromyl chloride, an inorganic chromate compound (e.g., potassium chromate, sodium chromate, ammonium chromate, potassium dichromate, sodium dichromate, or ammonium dichromate), or any combination thereof.

Aspect 78. A supported catalyst comprising:
a solid support; and
a chromate compound in an amount from about 0.1 to about 25 wt. % of chromium, based on the weight of the catalyst.

Aspect 79. The catalyst defined in aspect 78, wherein the chromate compound comprises potassium chromate, sodium chromate, ammonium chromate, potassium dichromate, sodium dichromate, ammonium dichromate, or any combination thereof.

Aspect 80. A supported catalyst comprising:
a solid support;
from about 0.1 to about 25 wt. % of chromium; and
from about 0.1 to about 25 wt. % of an alkali metal, based on the weight of the catalyst; wherein:
at least one bonding site on the chromium has a ligand characterized by the following formula: —O-Hydrocarbon group.

Aspect 81. The catalyst defined in aspect 80, wherein the molar ratio of the hydrocarbon group to chromium is in any suitable range or any range disclosed herein, e.g., from about 0.25:1 to about 2:1, from about 0.5:1 to about 2:1, from about 0.5:1 to about 1.5:1, from about 0.75:1 to about 1.75:1, or from about 0.75:1 to about 1.25:1.

Aspect 82. The catalyst defined in aspect 80 or 81, wherein the catalyst comprises chromium having an average valence of less than or equal to about 5.25, less than or equal to about 5, less than or equal to about 4.75, less than or equal to about 4.5, less than or equal to about 4.25, or less than or equal to about 4.

Aspect 83. The catalyst defined in any one of aspects 80-82, wherein an alkoxy group is bonded to the chromium.

Aspect 84. The catalyst defined in any one of aspects 78-83, wherein the solid support comprises any suitable solid support or any solid support disclosed herein, e.g., any support defined in any one of aspects 18-37, such as a solid oxide, a chemically-treated solid oxide, a zeolite, a clay, an activated carbon, or any combination thereof.

Aspect 85. The catalyst defined in any one of aspects 78-84, wherein the solid support comprises a silica-coated alumina having any suitable weight ratio of alumina to silica or a weight ratio in any range disclosed herein, e.g., from 1:20 to about 20:1, from about 1:5 to about 5:1, from about 3:1 to about 1:3, from about 1:1 to about 3:1, from about 1:1 to about 2:1, or from about 1.2:1 to about 1.8:1.

Aspect 86. The catalyst defined in any one of aspects 78-85, wherein the supported catalyst comprises any suitable amount of alkali metal or an amount in any range disclosed herein, e.g., from about 0.25 to about 15 wt. %, from about 0.5 to about 5 wt. %, from about 2 to about 20 wt. %, or from about 3 to about 15 wt. % of alkali metal, based on the weight of the supported catalyst.

Aspect 87. The catalyst defined in any one of aspects 78-86, wherein the supported catalyst comprises any suitable amount of chromium or an amount in any range disclosed herein, e.g., from about 0.25 to about 15 wt. %, from about 0.5 to about 5 wt. %, from about 2 to about 20 wt. %, or from about 3 to about 15 wt. % of chromium, based on the weight of the supported catalyst.

We claim:

1. A supported catalyst comprising:
a solid oxide comprising silica, silica-titania, silica-titania-magnesia, silica-coated alumina, or any combination thereof; and
an alkali metal chromate compound in an amount from about 0.1 to about 25 wt. % of chromium, based on the weight of the catalyst.

2. The catalyst of claim 1, wherein the chromate compound comprises potassium chromate.

3. The catalyst of claim 1, wherein the chromate compound comprises sodium chromate.

4. The catalyst of claim 1, wherein the chromate compound comprises potassium dichromate.

5. The catalyst of claim 1, wherein the chromate compound comprises sodium dichromate.

6. The catalyst of claim 1, wherein the catalyst contains from about 0.25 to about 15 wt. % chromium.

7. The catalyst of claim 1, wherein the catalyst further comprises from about 0.25 to about 15 wt. % alkali metal.

8. The catalyst of claim 1, wherein the catalyst has:
a total pore volume from about 0.1 to about 3 mL/g; and
a BET surface area from about 50 to about 700 $m^2/g$.

9. The catalyst of claim 1, wherein the solid oxide comprises silica.

10. The catalyst of claim 9, wherein the chromate compound comprises potassium chromate, sodium chromate, potassium dichromate, sodium dichromate, or any combination thereof.

11. The catalyst of claim 1, wherein the catalyst contains from about 3 to about 15 wt. % chromium.

12. The catalyst of claim 1, wherein the catalyst further comprises from about 3 to about 15 wt. % alkali metal.

13. The catalyst of claim 1, wherein:
the solid oxide comprises silica; and
the catalyst has:
a total pore volume from about 0.1 to about 3 mL/g; and
a BET surface area from about 50 to about 700 $m^2/g$.

14. The catalyst of claim 13, wherein the chromate compound comprises potassium chromate, sodium chromate, potassium dichromate, sodium dichromate, or any combination thereof.

15. A supported catalyst comprising:
a solid oxide comprising silica-coated alumina; and
a chromate compound in an amount from about 0.1 to about 25 wt. % of chromium, based on the weight of the catalyst.

16. The catalyst of claim 15, wherein the silica-coated alumina has a weight ratio of alumina to silica from about 1:5 to about 5:1.

17. The catalyst of claim 16, wherein the chromate compound comprises potassium chromate, sodium chromate, ammonium chromate, potassium dichromate, sodium dichromate, ammonium dichromate, or any combination thereof.

18. The catalyst of claim 17, wherein the weight ratio of alumina to silica is from about 1:3 to about 3:1.

19. The catalyst of claim 15, wherein the catalyst contains from about 0.25 to about 15 wt. % chromium.

20. The catalyst of claim 19, wherein the catalyst further comprises from about 0.25 to about 15 wt. % alkali metal.

21. The catalyst of claim 20, wherein the catalyst has:
a total pore volume from about 0.1 to about 3 mL/g; and
a BET surface area from about 50 to about 700 m$^2$/g.

22. The catalyst of claim 21, wherein the weight ratio of alumina to silica is from about 1:1 to about 2:1.

23. The catalyst of claim 22, wherein the chromate compound comprises potassium chromate, sodium chromate, potassium dichromate, sodium dichromate, or any combination thereof.

* * * * *